(12) United States Patent
Petit

(10) Patent No.: US 10,219,845 B2
(45) Date of Patent: Mar. 5, 2019

(54) DEVICE AND METHOD FOR SPINAL SURGERY

(75) Inventor: Dominique Petit, Verton (FR)

(73) Assignee: SAFE ORTHOPAEDICS, Eragny sur Oise (FR)

(*) Notice: Subject to any disclaimer, the term of this patent is extended or adjusted under 35 U.S.C. 154(b) by 0 days.

(21) Appl. No.: 13/518,949

(22) PCT Filed: Dec. 28, 2010

(86) PCT No.: PCT/FR2010/000880
§ 371 (c)(1),
(2), (4) Date: Sep. 24, 2012

(87) PCT Pub. No.: WO2011/080426
PCT Pub. Date: Jul. 7, 2011

(65) Prior Publication Data
US 2013/0012999 A1 Jan. 10, 2013

(30) Foreign Application Priority Data
Dec. 28, 2009 (FR) ..................................... 09 06369

(51) Int. Cl.
*A61B 50/30* (2016.01)
*A61B 17/70* (2006.01)
(Continued)

(52) U.S. Cl.
CPC ...... *A61B 17/7085* (2013.01); *A61B 17/7076* (2013.01); *A61B 17/7079* (2013.01);
(Continued)

(58) Field of Classification Search
CPC ............ A61B 17/7032; A61B 17/7076; A61B 17/708; A61B 17/8875; A61B 19/0271;
(Continued)

(56) References Cited

U.S. PATENT DOCUMENTS 5,591,167 A * 1/1997 Laurain et al. ............. 606/86 A
6,273,916 B1 8/2001 Murphy
(Continued)

FOREIGN PATENT DOCUMENTS

WO 9822035 A1 5/1998
WO 2005016183 A1 2/2005
(Continued)

OTHER PUBLICATIONS

Machine translation of WO98/22035, www.epo.org, generated Jul. 15, 2014, p. 1-9.*

*Primary Examiner* — Jacqueline T Johanas
(74) *Attorney, Agent, or Firm* — Bachman & LaPointe, P.C.

(57) ABSTRACT

Instrumentation for fixing at least two spinal vertebrae by pedicle screw type bone anchoring implants and connecting elements via the posterior or posterolateral approach has at least one bone anchoring element designed to be fixed to a vertebra, pre-mounted with a disposable mounting tube and a sterile sealed packaging. A kit of instruments for inserting or removing a spinal implant, has at least two threaded bone anchoring elements, a rod-type or plate-type connecting element mechanically connecting the bone anchoring elements and locking elements for locking the connecting element in position in relation to the anchoring elements, in order to perform all of the surgical procedures relating to the insertion or removal of the implant, all of the required instruments are disposable and packed in a sterile manner in one or several sealed packagings.

14 Claims, 17 Drawing Sheets

(51) Int. Cl.
*A61B 17/88* (2006.01)
*A61B 50/33* (2016.01)

(52) U.S. Cl.
CPC ...... *A61B 17/7091* (2013.01); *A61B 17/8875* (2013.01); *A61B 50/30* (2016.02); *A61B 50/33* (2016.02); *A61B 2050/3008* (2016.02)

(58) Field of Classification Search
CPC . A61B 17/1671; A61B 17/16; A61B 17/7086; A61B 2017/0023; B25B 23/1427
USPC .................. 606/60, 246, 254–279, 86 A, 99, 606/104–105; 206/370, 363, 366, 570, 206/477, 565
See application file for complete search history.

(56) References Cited

U.S. PATENT DOCUMENTS

| | | | |
|---|---|---|---|
| 7,189,244 B2* | 3/2007 | Newton et al. | 606/105 |
| 7,272,998 B1* | 9/2007 | Gauthier | B25B 23/141 |
| | | | 81/473 |
| 7,762,164 B2* | 7/2010 | Nino | B25B 15/02 |
| | | | 81/475 |
| 8,267,957 B1* | 9/2012 | Silver | 606/205 |
| 8,491,590 B2* | 7/2013 | Stad et al. | 606/90 |
| 8,795,283 B2* | 8/2014 | Petit | 606/86 A |
| 10,070,901 B2* | 9/2018 | Sandstrom | A61B 17/7086 |
| 2004/0024411 A1* | 2/2004 | Newton et al. | 606/105 |
| 2004/0138662 A1 | 7/2004 | Landry et al. | |
| 2005/0033430 A1* | 2/2005 | Powers et al. | 623/17.11 |
| 2005/0182401 A1* | 8/2005 | Timm et al. | 606/61 |
| 2005/0182409 A1* | 8/2005 | Callahan et al. | 606/72 |
| 2005/0192570 A1 | 9/2005 | Jackson | |
| 2006/0016300 A1* | 1/2006 | Bubel | A61B 17/8875 |
| | | | 81/475 |
| 2006/0241627 A1* | 10/2006 | Reo | 606/79 |
| 2007/0043356 A1* | 2/2007 | Timm et al. | 606/61 |
| 2007/0093847 A1* | 4/2007 | Scribner et al. | 606/93 |
| 2007/0162124 A1* | 7/2007 | Whittaker | 623/13.14 |
| 2007/0219558 A1* | 9/2007 | Deutsch | 606/72 |
| 2008/0087146 A1* | 4/2008 | Gao | B25B 15/02 |
| | | | 81/474 |
| 2008/0262318 A1 | 10/2008 | Gorek et al. | |
| 2008/0287995 A1* | 11/2008 | Gauthier | 606/246 |
| 2009/0171391 A1* | 7/2009 | Hutton et al. | 606/246 |
| 2009/0222045 A1 | 9/2009 | Gorek | |
| 2009/0259262 A1* | 10/2009 | Nayet | 606/86 A |
| 2010/0268242 A1* | 10/2010 | Ciccone et al. | 606/104 |
| 2010/0275746 A1* | 11/2010 | Wengreen | A61B 17/8875 |
| | | | 81/477 |
| 2010/0331896 A1* | 12/2010 | Le Couedic et al. | 606/305 |
| 2011/0184425 A1* | 7/2011 | Cheraux | A61B 17/8875 |
| | | | 606/104 |
| 2011/0218573 A1* | 9/2011 | Ferree | 606/263 |
| 2012/0031792 A1* | 2/2012 | Petit | 206/438 |
| 2012/0055296 A1* | 3/2012 | Landowski | B25B 23/1427 |
| | | | 81/474 |
| 2012/0078306 A1* | 3/2012 | Lynch | 606/264 |
| 2014/0172446 A1* | 6/2014 | Dumouchel | 705/2 |
| 2016/0095641 A1* | 4/2016 | Adamiec | B25B 23/141 |
| | | | 606/104 |
| 2016/0354906 A1* | 12/2016 | Nino | A61B 17/8875 |
| 2017/0128116 A1* | 5/2017 | Hansell | A61B 17/8875 |

FOREIGN PATENT DOCUMENTS

| | | |
|---|---|---|
| WO | 2006002430 A2 | 1/2006 |
| WO | 2007092870 A2 | 8/2007 |
| WO | 2008097974 A2 | 8/2008 |

\* cited by examiner

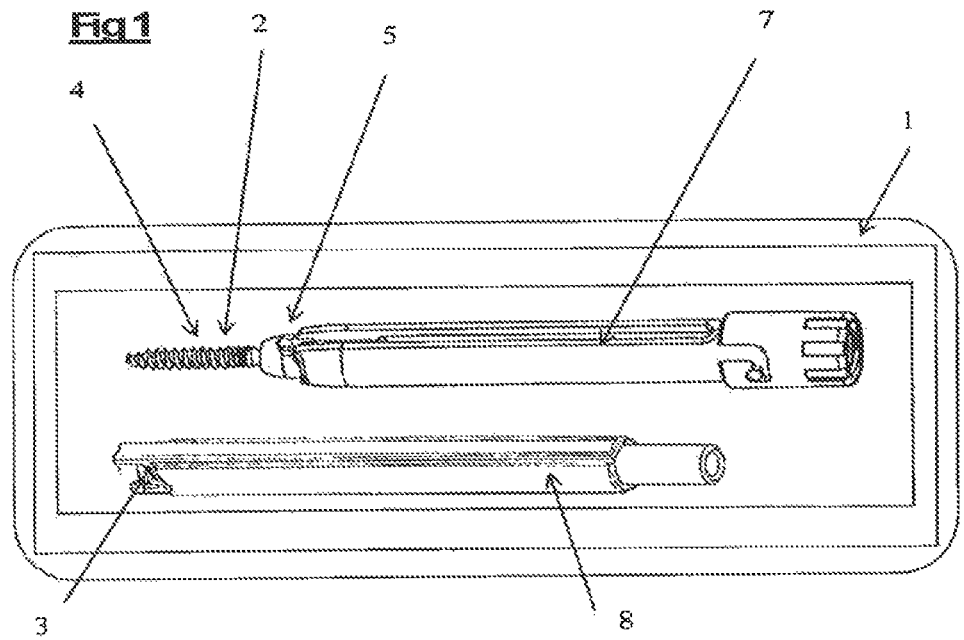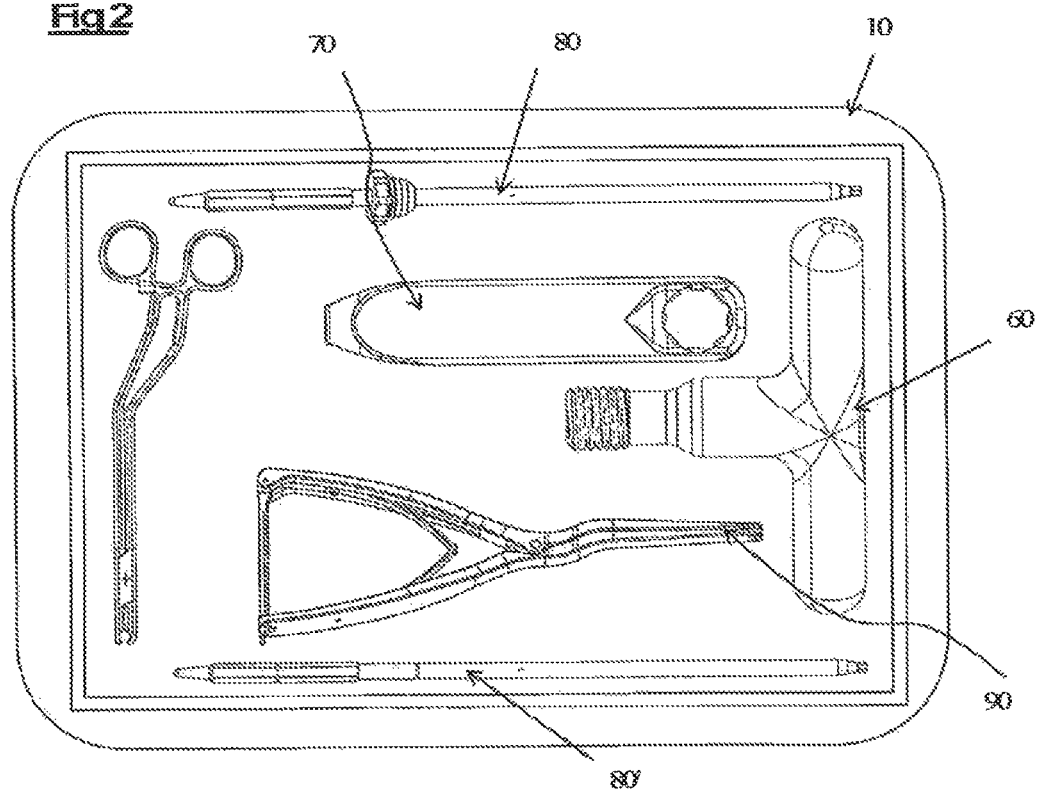

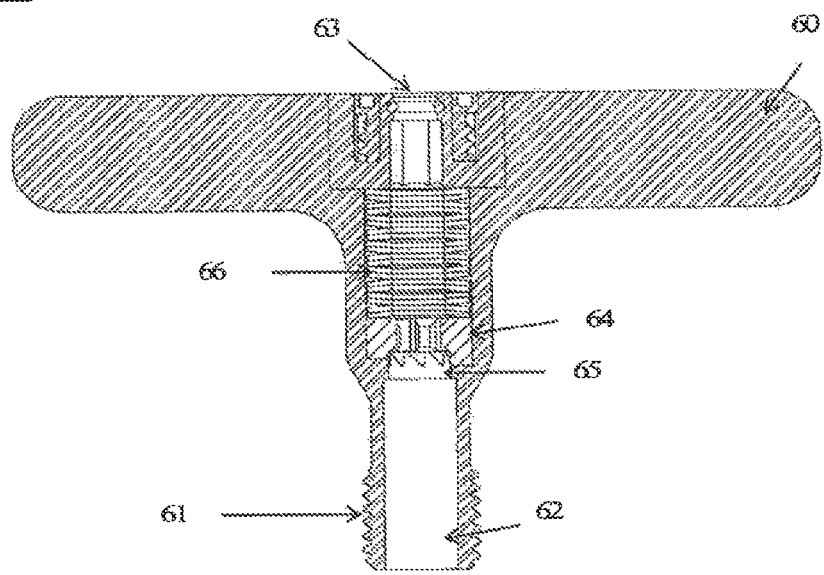
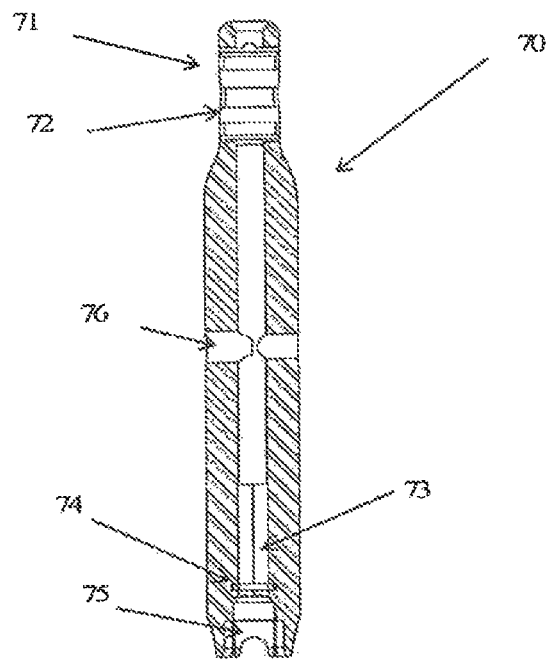

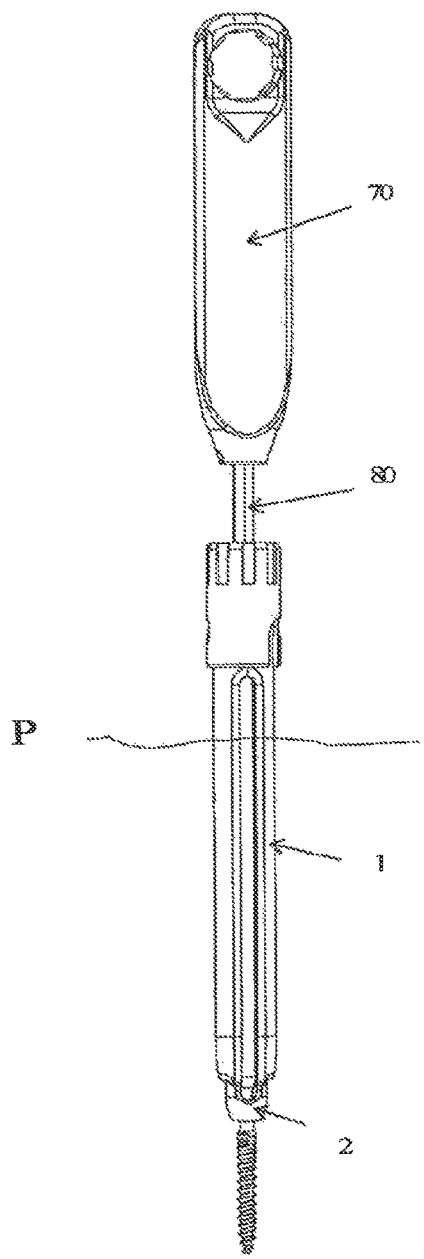
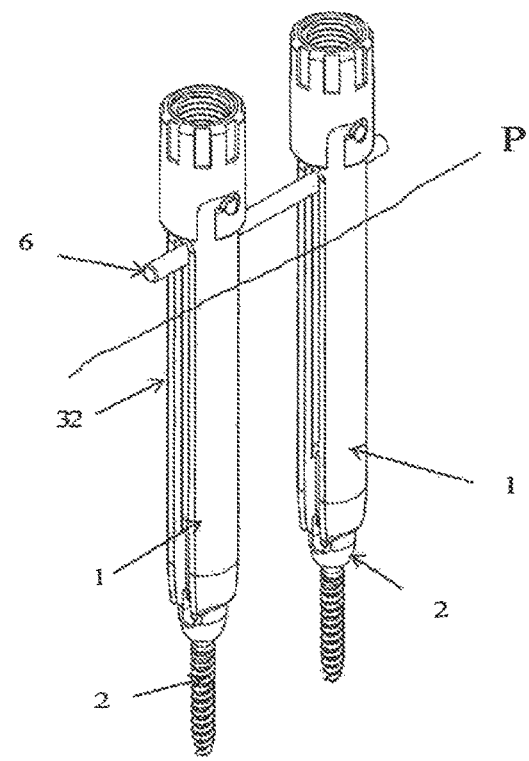

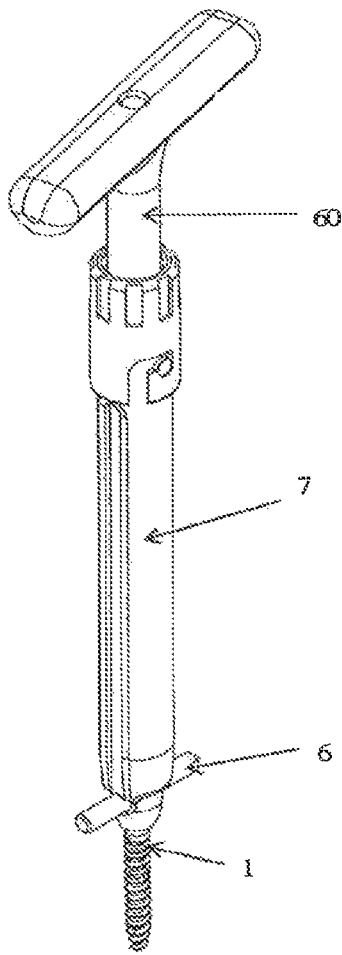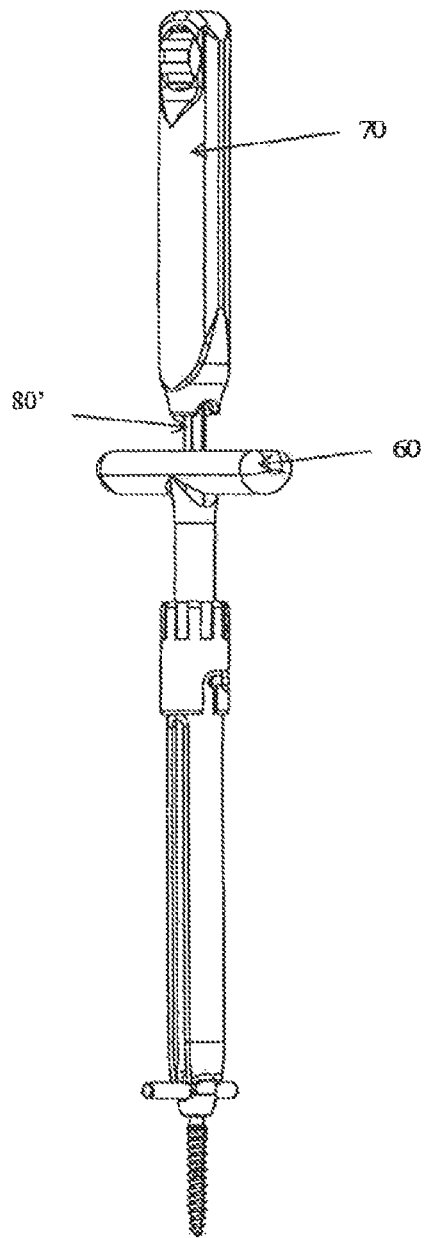

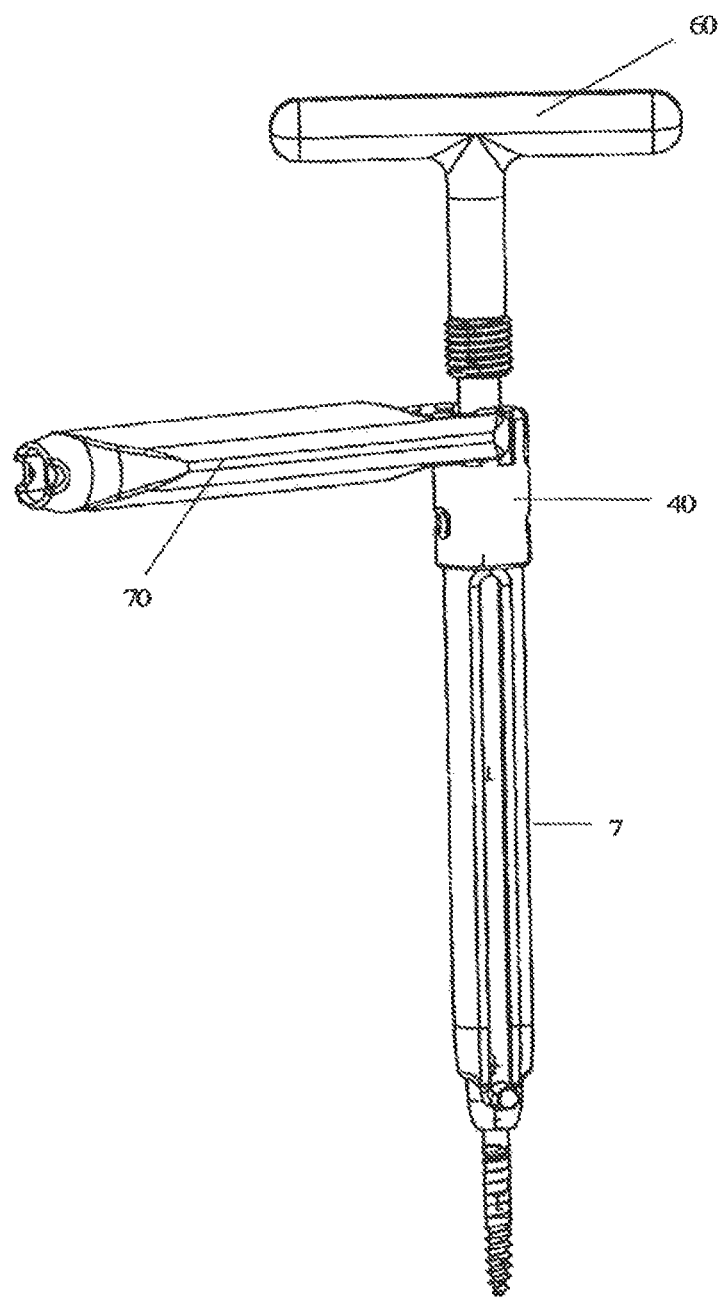

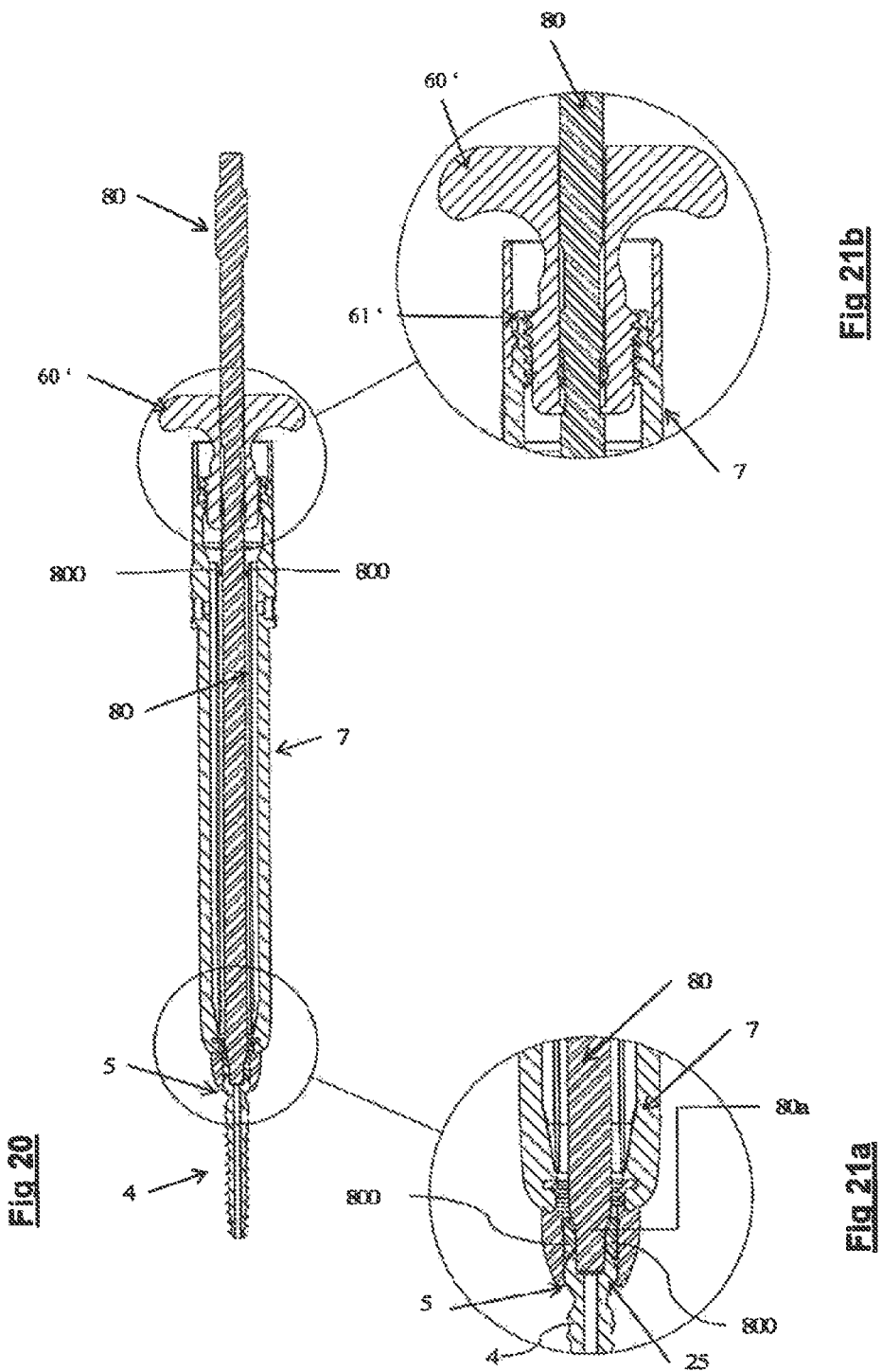

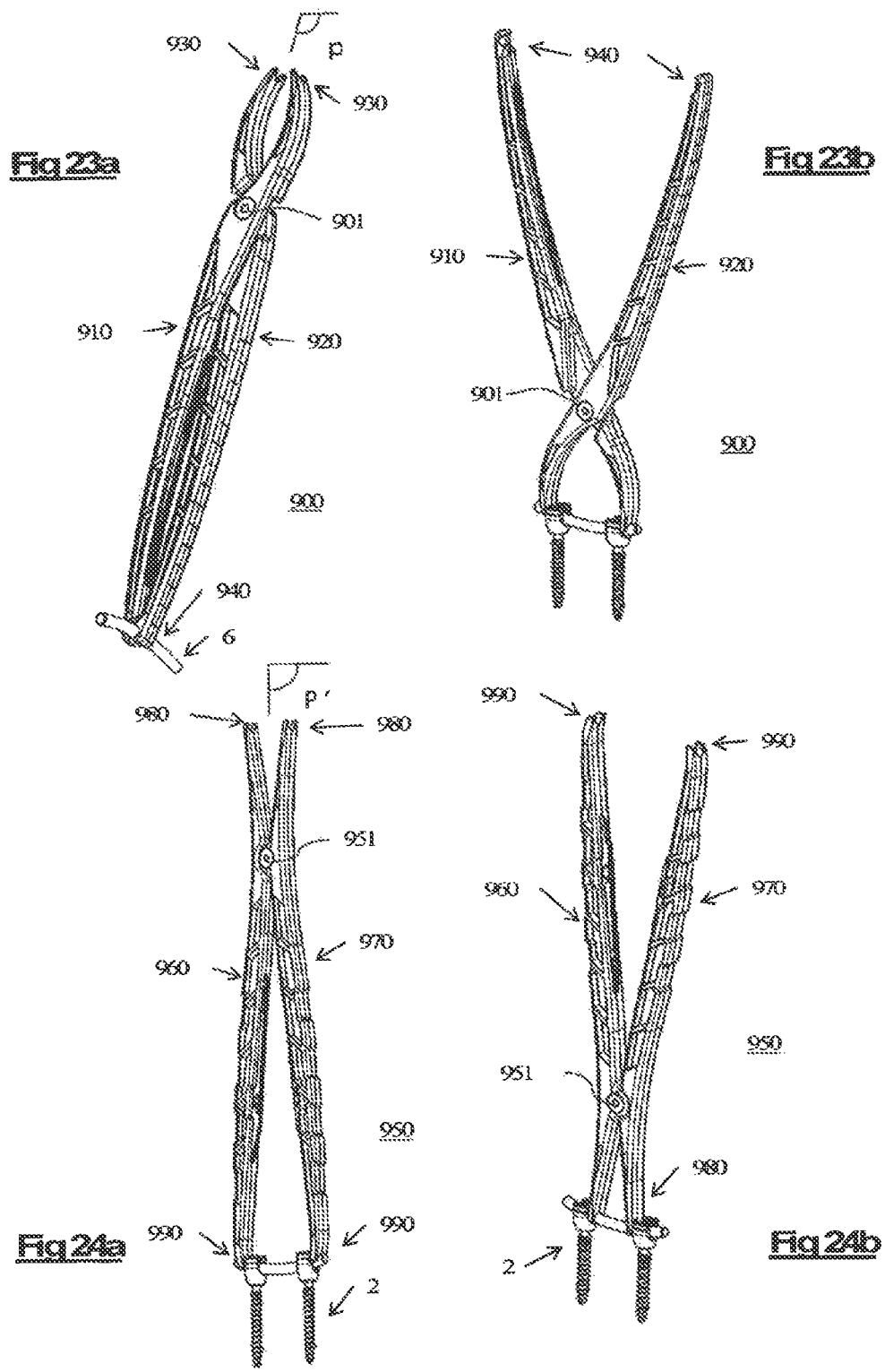

DEVICE AND METHOD FOR SPINAL SURGERY

BACKGROUND

The invention relates to a device allowing performance of spinal stabilisation by a screw-type bone anchoring element via the posterior or posterolateral approaches.

The device according to the invention is designed particularly, but not exclusively, for lumbar, thoracic or furthermore posterior cervical spinal osteosynthesis via minimally invasive or open surgical approaches.

In the conventional method in itself, in case of anatomical dysfunctions of the vertebral column, pedicle screw-type bone anchoring elements are inserted (installed) in the vertebrae, interconnected by rod-type or plate-type connecting elements.

The state of the art in the field of vertebral column surgery involves providing hospitals with implants and sets of instruments for their insertion (installation). Some companies specialised in the field supply ready-to-use, sterile packed implants. The sets of instruments reusable after decontamination and sterilisation present many disadvantages. The risk of interpatient contamination is very high; cleaning, decontamination and sterilisation are steps which are sometimes almost impossible to perform correctly in view of complex designs with many cavities inside the instruments. These steps are a financial burden for the hospitals and represent very high costs, both in human and material terms.

Loss, breakage, wear and damage of an instrument may result in disastrous consequences for the patient or even cause cancellation of the surgery. The logistics also present many disadvantages; cumbersome and costly both for the industrialist and the hospital, they most often involve significant inventories. Indeed, since surgeons only operate two days a week in the majority of cases, the number of sets of instruments made available to the hospital depends on the activity, with traumatology operations being added if necessary to the surgical programme.

The rotations of sets between the hospital and the industrialist's logistics service are therefore very large in number, which significantly increases the risks of losses and errors.

In other surgical fields, in order to take account of the safety aspect both for the patient and surgeon, the financial, human and material aspect for the hospital in addition to the service offered and expected by the industrialist's customers, it has been proposed to shift towards disposable "all sterile" surgery. International application WO 98/22035 is known for example. The latter describes a kit of surgical instruments, manufactured economically from synthetic sterile material. This type of kit is marketed for genecological or microsurgical operations. These generic instruments of the scissor, dissection plier or furthermore scalpel type are not intended for insertion of an orthopedic implant and are not caused to undergo high mechanical stresses. Transformation of a metallic instrument to disposable polymer is known in many medical fields.

International application WO 2005/016183 is also known. It describes an implant kit of the vertebral plate and screw type combined with disposable sterile packed instruments. Apart from the disadvantage of only offering a single screw length and diameter for the bone anchoring, this method only describes a single type of instrument: a screwdriver shank and its handle. This international application does not offer any technical solution for designing and manufacturing instruments subject to major stresses such as the vertebral distracter which is absolutely essential for inserting the implant.

SUMMARY OF THE INVENTION

The present invention intends to solve in their entirety the problems associated with use of polymer materials for manufacturing sterile packed disposable surgical instruments and more specifically of the pedicle screw type for spinal surgery.

To this end and according to a first aspect, the invention proposes a pre-mounted pedicle screw-type bone anchoring element with a multifunctional mounting tube, all prepared at the factory in disposable sterile sealed packaging. More specifically, it refers to a spinal device for fixing vertebrae via the posterior or posterolateral approach, characterised in that said device comprises at least:

a bone anchoring element of the pedicle or vertebral screw type, comprising a proximal portion equipped with an interface for attaching a rod-type or plate-type connecting element and a threaded distal portion, a mounting tube interdependently pre-mounted on the bone anchoring element, said tube being removable from the bone anchoring element, a sterile sealed packaging of the bone anchoring element and the pre-mounted mounting tube.

According to one embodiment, the mounting tube comprises a longitudinal opening, emerging in the proximal portion of the bone anchoring element for passage of the connecting element.

Advantageously, the pre-mounted tubes are removable after implantation of the bone anchoring element and its locking element.

According to one embodiment, the internal diameter of the mounting tube allows passage of a locking element for locking the connecting element on the bone anchoring element.

According to one embodiment, the internal diameter of the mounting tube allows passage of accessories for positioning a locking element.

Advantageously, the device comprises an accessory passing through the mounting tube and having one end pre-mounted on the bone anchoring element.

Advantageously, the mounting tube is equipped with means of retaining the accessory in alignment with the bone anchoring element. According to a specific configuration, the means of retention comprise lugs arranged on the internal face of the mounting tube. Provision may be made, in addition to or in exchange for the lugs, for a retaining fin installed on the distal end of the mounting tube in order to retain the accessory in a given position in relation to the mounting tube and the bone anchoring element.

According to a particular variant, the mounting tube is provided with at least one dovetail in its internal passage which is complementary with the accessory for positioning of the locking element in order to obtain a sufficiently resistant interconnection with regard to the stresses exerted on this assembly.

According to one embodiment, the mounting tube is made of composite, polymer, ferrous or non-ferrous alloy material or furthermore a combination of these different materials.

According to one embodiment, the mounting tube is overmoulded on the bone anchoring element.

According to one embodiment, the mounting tube is made of one or several materials, with at least one of said materials being incompatible with an autoclave sterilisation cycle involving a holding phase at 134° C. for 18 minutes.

According to one embodiment, the distal end of the mounting tube comprises an indentation for positioning a handle-type perpendicular retaining element. This perpendicular retaining element is mainly used during tightening of the locking element with a counter-torque effect, thereby avoiding rotation of the assembly of the bone anchoring element and the mounting tube.

According to one embodiment, the distal end of the mounting tube comprises a threaded or tapped area. This thread or tap is designed to receive a pushing element of the locking element holding tube described below.

According to one embodiment, the mounting tube consists of two half-shells.

According to one embodiment, the two half-shells are identical.

According to one embodiment, the distal portions of the two half-shells are contiguous.

According to one embodiment, the continuous portions of the two half-shells comprise a mortise and tenon positioning means, or similar locating means in order to ensure proper positioning of these two half-shells.

According to one embodiment, the two half-shells are adhesively bonded, welded or clipped.

According to a particular variant, the proximal connection of the half-shell on the bone anchoring element is provided by an indentation complementary with the shape of this half-shell such that assembly or disassembly is performed by rotating the half-shell around the bone anchoring element.

According to this particular variant, once the distal portions of the two half-shells have been interconnected, it is impossible to separate the latter from the bone anchoring element, while allowing easy disassembly when the two half-shells are disconnected.

According to one embodiment, the two half-shells are interdependently retained, preferably by means of a ring on the distal end of said half-shells.

Advantageously and according to this particular variant, the distal portion of this ring is equipped with a thread and a indentation. This thread is designed to receive a pushing element of the locking element holding tube and the indentation is designed to receive a perpendicular retaining element.

According to one embodiment, the ring comprises at least one bayonet-type shape which interconnects with studs arranged on the two half-shells, thereby allowing easy and rapid assembly of said ring.

According to one embodiment, a compression spring is located between the ring and the two half-shells in order to guarantee a secure fit of the assembly.

According to one embodiment, the ring comprises at least one transverse spindle between the ring and the two half-shells.

According to one embodiment, the dimensioning of the spindle is defined such as to break under a shear load according to a given torque.

Advantageously, the mounting tube and the ring are arranged to form a rigid assembly.

Advantageously, the two half-shells are arranged to form a guide tube when retained interdependently with each other.

Advantageously, the two half-shells each have a proximal end arranged to lock into engagement with the bone anchoring element.

Advantageously and according to this particular variant, this breakage torque is identical to the tightening torque of the locking element which secures the rod connecting element in the bone anchoring element.

Advantageously and according to this particular variant, this breakage determines disassembly of the ring and therefore also of the two half-shells.

According to one embodiment, the locking element is interdependently pre-mounted with a locking element holding tube in order to form a locking assembly, with the locking element being removable from the locking element holding tube.

Advantageously, this retention is performed by a tap.

According to a particular variant, this tap may be slightly different from the thread of the locking element in order to ensure its retention by trapping.

According to a particular variant, the locking element is retained by a clipping.

Advantageously, the locking assembly can be sterile packed.

According to one embodiment, the locking assembly is sterile packed in the sealed packaging.

According to one embodiment, the locking element holding tube is of dimensions that allow its insertion into the mounting tube. The mounting tube may advantageously have a tubular internal wall provided with at least one locating relief, with the locking element holding tube having a complementary locating relief of a shape complementary with the locating relief of the mounting tube. The locking element holding tube may furthermore have a proximal portion provided with a bearing relief, located opposite the interdependence interface of the bone anchoring element when the locking element holding tube is inserted into the mounting tube, in order to rest a connecting element on the interdependence interface of the bone anchoring element. The device may furthermore comprise a pushing element interacting with the locking element holding tube for insertion of the locking element holding tube into the mounting tube.

Advantageously, the proximal end is equipped with two lugs on either side of the locking element, of a length at least equal to the height of the locking element in relation to the latter's face intended to come into contact with the rod. The width of these lugs cannot be greater than the diameter of the rod connecting element. The function of these two lugs is to allow bearing on the rod connecting element without any contact of the locking element either with the bone anchoring element or with the rod connecting element.

According to a particular variant, the external shape of the locking element holding tube is provided with two dovetails of a shape complementary with the two half-shells.

These complementary dovetails between the two half-shells and the locking element holding tube considerably reinforce the assembly, thereby avoiding any risk of separation of the two half-shells under high stresses and imparts greater mechanical resistance in flexion and torsion.

According to a particular variant, the total length of the locking element holding tube is greater than that of the two half-shells or furthermore of the two half-shells and of the ring.

According to this particular variant, the distal portion of the locking element holding tube and the internal shape of the pushing element are compatible with positioning the rod connecting element at the bottom of the U-shaped housing provided of the bone anchoring element. The locking element holding tube therefore also serves as a rod pusher.

According to one embodiment, the pushing element comprises a thread or a tap which interacts with the threaded or tapped area of the mounting tube for positioning of the connecting element.

Advantageously, the mounting tube, when the locking element holding tube is positioned inside it, forms a guide tube.

Advantageously, the mounting tube and the locking element holding tube, when it is positioned inside it, form a rigid assembly.

According to one embodiment, the locking element holding tube has an internal shape allowing passage of a screwdriver for tightening or untightening the locking element.

According to one embodiment, the locking element holding tube is made of composite, polymer, ferrous or non-ferrous alloy material or furthermore a combination of these different materials.

According to one embodiment, all the components of the device are disposable.

According to one embodiment, all the components of the device are packed in a sterile manner in one or several sealed packagings.

In the above, emphasis has been placed on the existence of a sterile packaging for the bone anchoring element and the pre-mounted mounting tube. According to another aspect of the invention however, the latter also covers the mechanical characteristics of the tube and its fixing to the bone anchoring element, regardless of their sterile packaging. Hence, the invention also refers to a spinal device for fixing vertebrae via the posterior or posterolateral approach, comprising an anchoring element and a tube and distinguished by one or several of the characteristics described above, considered individually or in combination.

According to another aspect of the invention, the latter refers to a kit of instruments for inserting or removing a spinal implant, comprising at least two threaded bone anchoring elements, a rod-type or plate-type connecting element mechanically connecting the bone anchoring elements and locking elements for locking the connecting element in position in relation to the anchoring elements, in order to perform all of the surgical procedures relating to the insertion or removal of said implant, characterised in that all of said required instruments are disposable and packed in a sterile manner in one or several sealed packagings.

According to a particular variant, the kit of instruments is reduced for insertion or removal of the implants. It mainly consists of two screwdriver shanks (bone anchoring element and locking element), two multifunctional handles, rod holding plier and compression-distraction plier, i.e. a total of six elements.

Advantageously, the instrumentation kit for insertion or removal of the implants only consists of six instruments owing to their multifunctional designs and the mounting tubes and locking element holding element parts pre-mounted on said implants.

Advantageously and according to a particular variant, the invention proposes control of the tightening torque of the locking element in order to secure retention of the rod connecting element on the pedicle screw-type bone anchoring elements.

Advantageously, the invention offers the surgeon a choice of surgical approach, by a minimally invasive approach or by conventional open surgery.

According to one embodiment, the instruments are made of composite, polymer, ferrous or non-ferrous alloy material or furthermore a combination of these different materials.

According to one embodiment, the disposal instrument device comprises at least one screwdriver shank, a handle and a pair of plier.

According to one embodiment, the kit comprises a "T"-shaped handle equipped with a torque limiter for final torque tightening of the locking element. The tightening torque of the locking element is optimum in order to guarantee retention of the rod connecting element in the bone anchoring element.

Advantageously, the pushing element of the locking element holding tube/rod introducer is also the T-shaped handle which is equipped with a thread corresponding to that of the distal end of the two half-shells or of the ring.

Advantageously, this T-shaped handle is designed to receive two screwdriver shanks for the bone anchoring element and the locking element.

Advantageously, this T-shaped handle is cannulated over its entire length allowing passage of the screwdriver shanks.

According to this particular configuration, the proximal meshing portions of the pedicle screw and stopper screwdriver shanks are different.

According to this particular configuration, the torque function of this T-shaped handle is only applicable to the shank of the screwdriver for tightening the locking element.

According to one embodiment, the kit comprises a straight handle allowing positioning or disassembly of the bone anchoring elements, temporary tightening or untightening of the locking elements and perpendicular retention of the device.

Advantageously, this straight handle is designed to receive the different screwdriver shanks (pedicle screw and stopper).

Advantageously, this straight handle is cannulated over its entire length allowing passage of the different screwdriver shanks.

Advantageously, provision can also be made for the straight handle also allowing use as a T for positioning or disassembly of the bone anchoring elements and tightening or untightening of the locking elements, such that a greater torque is easier to apply.

Advantageously, the perpendicular retaining element is also the straight handle. One of the ends of the latter is provided with a indentation complementary with that of the distal end of the two half-shells or the ring.

According to one embodiment, the straight handle may be arranged to allow retention of the bone anchoring element for tightening or untightening the locking elements. One of the ends of this straight handle is provided with a shape complementary with the head of the bone anchoring element.

Advantageously, this straight handle therefore allows, during tightening or untightening of the locking element, exertion of an counter-torque effect both when the two half-shells or half-shells+ring are in position and when the latter are disassembled.

According to one embodiment, the straight handle may also allow gripping the locking element and guiding the latter on the bone anchoring element. This grip is arranged in order to securely retain the locking element in its end near the shape complementary with the head of the bone anchoring implant.

Advantageously, this retention is performed by a tap.

According to a particular variant, this tap may be slightly different from the thread of the locking element in order to ensure its retention by trapping.

According to a particular variant, the locking element is retained by a clipping.

Advantageously, the kit of instruments comprises plier for compression and plier for distraction of the bone anchoring elements, with the compression plier and distraction plier only forming a single pair of pliers.

According to one embodiment, the manoeuvring plier comprise two arms allowing compression and distraction of the bone anchoring elements. This two-armed manoeuvring plier may comprise curved proximal ends with notching on the convex portions.

Advantageously, this two-armed manoeuvring plier comprises curved proximal ends with longitudinal positive location (indexation). The positive location can be performed by a groove on one of the arms and a protruding stud on the other arm.

Advantageously, the kit of instruments may include a plier (900) comprising two crossed arms symmetrical in relation to a reference plane and fixed to each other by means of a joint, wherein each arm has a fork-shaped end to overlap a rod, said fork-shaped ends of each arm being arranged facing each other in relation to the plane of symmetry, wherein the ends of the arms form compression ends and wherein the ends opposite the compression ends of each arm are arranged to allow gripping of the rod during a movement in which the compression ends are moved towards each other.

The kit of instruments may also include a plier comprising two crossed arms symmetrical in relation to a reference plane and joined to each other by means of a joint, wherein each arm has first and second fork-shaped ends to overlap a rod, wherein one of the ends of one of the arms is arranged with the end of the other arm positioned opposite the former arm in relation to the plane of symmetry in order to form distraction ends and wherein the other ends form compression ends.

According to another aspect of the invention, the latter refers to an operation of inserting or removing a spinal implant, comprising at least two threaded bone anchoring elements, a rod-type or plate-type connecting element mechanically connecting the bone anchoring elements and locking elements for locking the connecting element in position in relation to the anchoring elements, characterised in that the instruments interacting with the bone anchoring elements and the locking elements during insertion or removal of the implant are taken from one or several sealed sterile packagings at the beginning of the operation and are discarded at the end of the operation without being sterilised again.

BRIEF DESCRIPTION OF THE DRAWINGS

Other aims and advantages of the invention will appear in the course of the following description, made with reference to the appended drawings in which:

FIG. 1 represents a diagrammatic view of a device according to a first embodiment of the invention;

FIG. 2 represents a diagrammatic view of the kit of instruments according to a first example of embodiment;

FIG. 8 represents a cross-section of the multifunctional T-shaped handle in its torque version;

FIG. 9 represents a cross-section of the multifunctional straight handle;

FIGS. 10*a* to 10*g* represent the differing operating steps for positioning the bone anchoring element, the rod connecting element and the locking element;

FIG. 20 represents a cross-sectional view along the axis XX-XX of the tube/screwdriver assembly in FIG. 15 on which the bone anchoring element is pre-mounted;

FIGS. 21*a* and 21*b* respectively represent a detailed view of the proximal end and of the distal end of the tube illustrated in FIG. 20.

FIGS. 23*a* and 23*b* represent a compression plier contained in the kit of instruments in FIG. 16, said compression plier being illustrated according to two situations of use;

FIGS. 24*a* and 24*b* represent a distraction plier contained in the kit of instruments in FIG. 16, said distraction plier being illustrated according to two situations of use.

For greater clarity, identical or similar elements of the different embodiments are marked by identical reference signs on all the figures.

DETAILED DESCRIPTION OF THE PREFERRED EMBODIMENT(S)

Figure 3A:
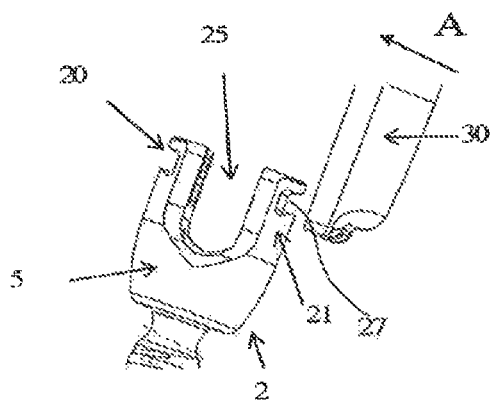
FIGS. 3*a* and 3*b* represent the connection between the bone anchoring element and the multifunctional mounting tube.

With reference to FIG. 1, a device (1) designed to be fixed on to a vertebra is described, comprising a means of bone anchoring (2) and its means of closure (3), respectively interdependently pre-mounted on tubes (7) and (8), all prepared at the factory in disposable sterile sealed packaging.

In order to facilitate reading of that which follows, the device 1 described above will subsequently be referred to as "screw device (1)".

In a specific configuration not illustrated, the screw device (1) may comprise several means of bone anchoring (2) and several means of closure (3) interdependently pre-mounted on disposable tubes (7) and (8), all in a same disposable sterile sealed packaging.

The means of bone anchoring (2) consists of a threaded portion (4) designed to be inserted into the bone and a head portion (5) intended to receive a rod-type or plate-type connecting element (6).

In order to facilitate reading of that which follows, the bone anchoring element (2) will subsequently be known as "screw (2)", the head portion (5) will be subsequently known as "head of the screw (5)", the rod-type or plate-type connecting element (6) will subsequently be known as "rod (6)" and the locking element (3) will subsequently be known as "stopper (3)". The screw (2), rod (6) and stopper (3) assembly will subsequently be known as the "implant".

In a specific configuration, the head of the screw (5) is arranged with a U shape (25) provided with a channel designed to receive the rod (6). Advantageously, the channel is bordered by two branches provided with an internal tap (26) designed to receive the stopper (3) in order to attach the screw (2) and the rod (6). The threaded portion (4) of the screw (5) may be fixed or mobile in relation to the head of the screw (5); this type of screw (5) with a stopper (3) forms part of the public domain and constitutes one of the states-of-the-art of spinal surgery for fixing vertebrae.

The most frequently used material for manufacturing implants is titanium. In a specific configuration of the invention, the material used for manufacture may be any implantable material known or unknown to date, such as Peek, stainless steel, cobalt chrome or furthermore a composite based on fibreglass or carbon. Coatings of the HATCP type (HydroxyApatite TriCalcium Phosphate) or others may also be applied in order to improve bone anchoring or the overall mechanical resistance of the implant.

The disposable tubes (7) and (8) may be manufactured from any material known or unknown to date, such as composites, polymers and ferrous and non-ferrous metals (aluminium) as long as they fulfil the biocompatibility criteria related to the application. Preferably, the material used will be recyclable in order to comply with environmental protection requirements. Coatings may also be applied in order to fulfil the biocompatibility criteria or furthermore enhance the mechanical characteristics.

Preferably at least one of said materials forming the device (1) is incompatible with an autoclave sterilisation cycle involving a holding phase at 134° C. for 18 minutes.

The chosen sterilisation method will be compatible depending on the characteristics of said materials according to the state of the art. This sterilisation will be preferably performed by gamma irradiation or furthermore according to a specific process using ethylene oxide (ETO).

FIG. 2 also describes a kit of instruments (10) for disposable use, sterile packed for inserting or removing implants. Totaling six instruments in this particular configuration, they make it possible to perform all of the surgical procedures required for inserting or removing implants. Advantageously, the materials or coatings used for manufacturing this kit of instruments (10) are the same as those which may be used for manufacturing the tubes (7) and (8).

This device of a kit of instruments (10) offers many advantages such as that of reducing the overall cost of spinal surgery and guaranteeing no interpatient contamination, thereby significantly reducing the number of nosocomial infections.

This device of the kit of instruments (10) is mainly composed of screwdriver shanks, handles and pliers.

Advantageously, non-limitatively and non-restrictively, the kit of instruments (10) makes it possible to perform the following surgical procedures: insertion of the screws (2) in the pedicles of the vertebrae, arching of the rod (6) in order to conform to the patient's anatomy, insertion of the rod (6) regardless of the introduction forces, positioning of the stopper (3), correction manoeuvres of the instrumented vertebrae of the compression and distraction type and controlled and secure final tightening of the stopper (3).

Advantageously and according to a particular configuration, the kit of instruments (10) includes trial rods allowing the surgeon to determine the optimum length and curvature before the choice of rods (6) to be implanted.

Advantageously, the same kit of instruments (10) may be used for removing the equipment after osteosynthesis, or for any other clinical reasons.

Advantageously, many instruments making up this kit (10) are multifunctional. All the characteristics will be subsequently described in detail.

Advantageously, the tubes (7) and (8) respectively pre-mounted on the screw (2) and the stopper (3) are also multifunctional.

Advantageously, the combination of the kit of instruments (10) and pre-mounted tubes (7) and (8) offers the surgeon a choice of surgical approach, either by a median, lateral or bilateral minimally invasive approach or by conventional open surgery.

Figure 3B:
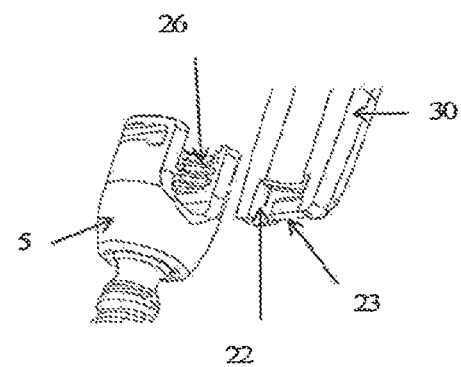

FIGS. 3a and 3b describe in the preferred embodiment the fixing of the mounting tube (7) on the screw (2).

The external surface of the head of the screw (5) comprises two indentations (20) arranged on either side of the U-shaped channel (25). The indentation is made up of a channel (27) and an internal housing (21). In this configuration, the mounting tube (7) consists of two half-shells (30, 31). The female shape of the indentation on the head of the screw (5) is reproduced in male form on the proximal ends of the half-shells (30 and 31). Advantageously, the male external shape of the head of the screw (5) is reproduced in female internal form (22) on the proximal end of the two half-shells in order to strengthen and consolidate the two half-shells (30 and 31) and the screw (2) in all directions (except that of rotation with the internal indentation (21) as the centre of rotation).

More particularly, the proximal end of each half-shell has a cavity with a shape complementary to the shape of one of the branches of the head of the screw (5). Hence, when the two half-shells (30, 31) are installed on the head of the screw (5), the branches of the latter are trapped in the cavities arranged on each of the proximal ends of the half-shells, with the wall bordering each cavity appreciably "hugging" the external surface of the branches of the head of the screw (5). Advantageously, the cavity of each proximal end comprises a lug arranged such that when the proximal ends are placed on the head of the screw (5), the lug engages in the indentation arranged on the head of the screw. In the embodiment illustrated, the recesses are arranged on the upper end of the head of the screw (5).

Figure 4A:
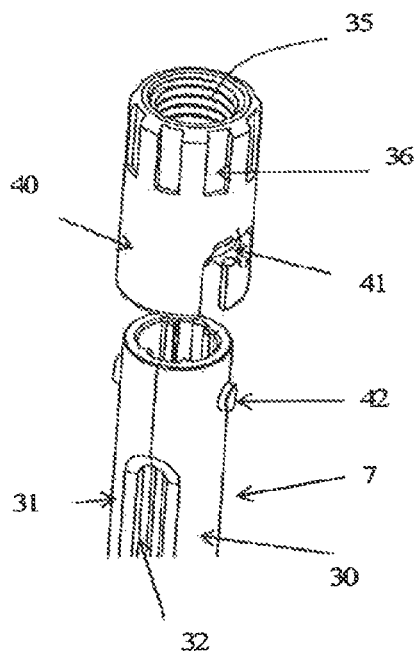
FIGS. 4*a* and 4*b* represent different assemblies of the ring on the two half-shells forming the multifunctional mounting tube.
Figure 4B:
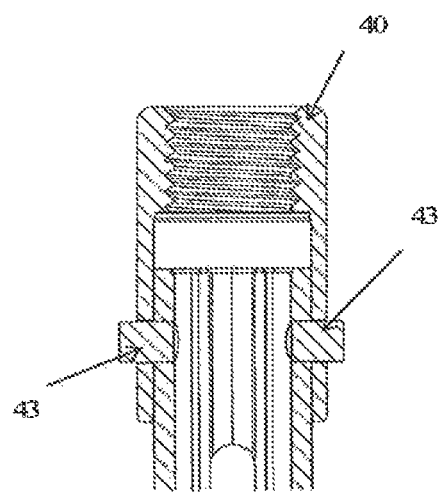
Figure 5:
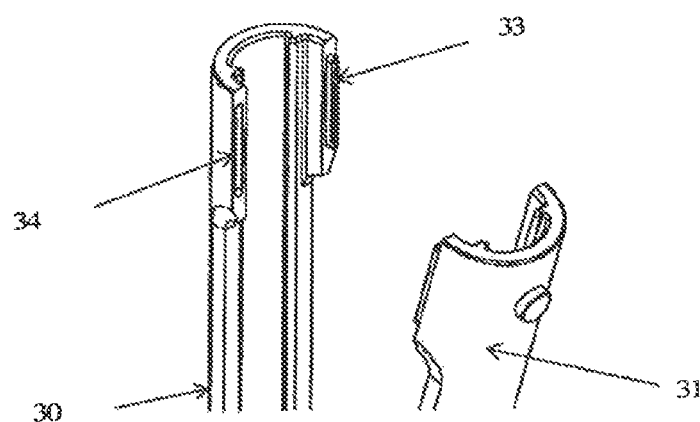
FIG. 5 represents a specific assembly of the two half-shells forming the multifunctional mounting tube.
Figure 6:
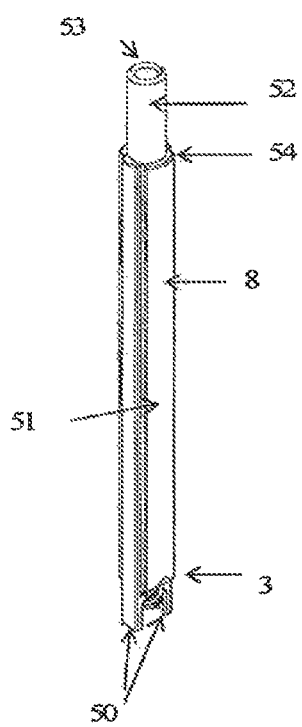
FIG. 6 represents the locking element holding tube.

It is of course obvious that the invention is not limited with regard to the means of retention of the implant to the mounting tube and the lugs as illustrated in FIGS. 4 to 6, with the possibility of making provision for all other forms of lugs or all other means of retention of the implant without departing from the framework of the invention.

Advantageously, the internal housing (21) is arranged to allow positioning of the half-shell by pivoting/rotating the latter on the head of the screw (5) according to direction (A) with the internal housing (21) as the rotation point. This form of male/female indentation with an internal housing (21) offers the advantage of being non-removable when the distal portions of the two half-shells are contiguous (FIG. 4a) and allows easy disassembly when these two half-shells (30 and 31) are no longer contiguous (FIG. 5).

Figure 3C:
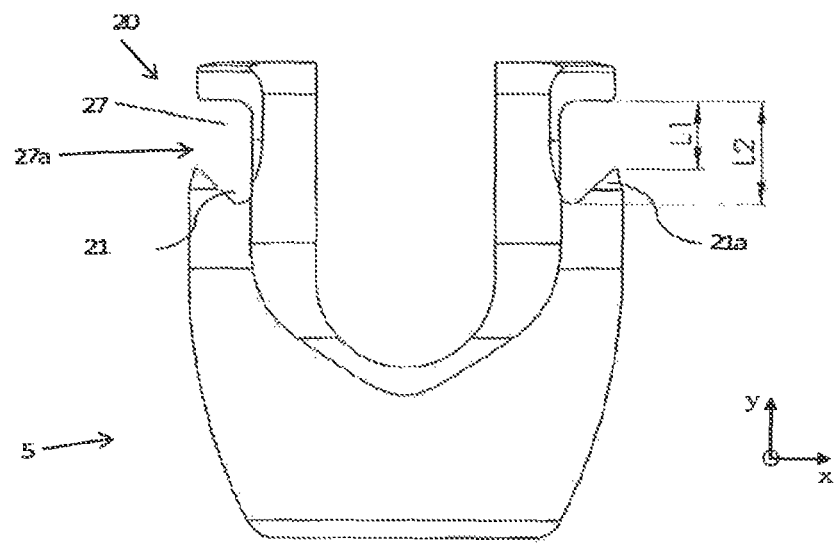
FIG. 3*c* represents a detail of the connection between the bone anchoring element and the multifunctional mounting tube illustrated in FIG. 3*a*.
Figure 3D:
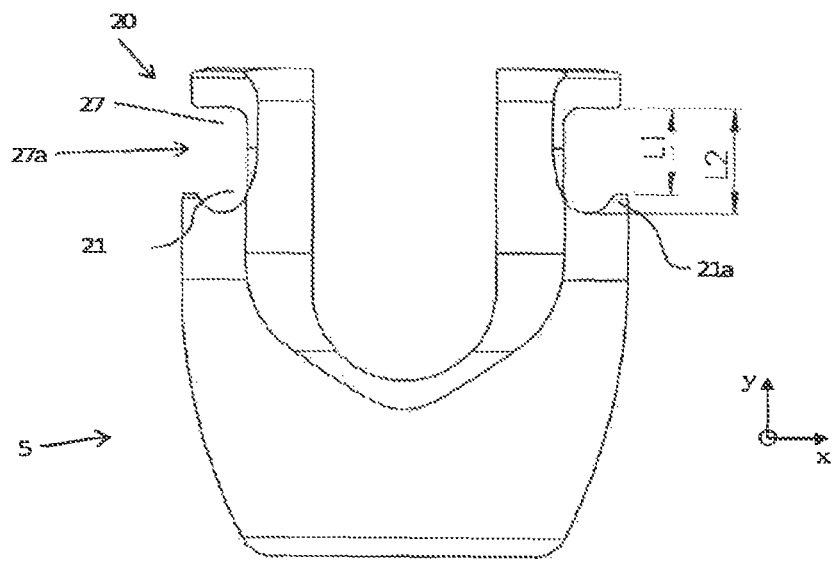
FIG. 3*d* represents a detail of a connection between the bone anchoring element and the multifunctional mounting tube according to an embodiment variant.

FIGS. 3c and 3d respectively illustrate two examples of shape of indentations. In the two examples illustrated, the channel (27) forms together with the housing (21) a receiving cavity having an internal height L2 greater than the height L1 of the entrance opening (27a). This dimensional difference allows locking of the proximal end of the mounting tube (7) on the head of the screw (5), at least in translation along the axes (x, y).

In the embodiment illustrated, the dimensional difference is borne on the bottom of the indentation under the entrance opening (27a) in order to allow disassembly of the half-shells (7) by pivoting the latter on the lower bearing edge (21a) bordering the entrance opening (27a).

In one particular configuration, the mounting tube (7) is overmoulded on the screw.

Figure 10C:
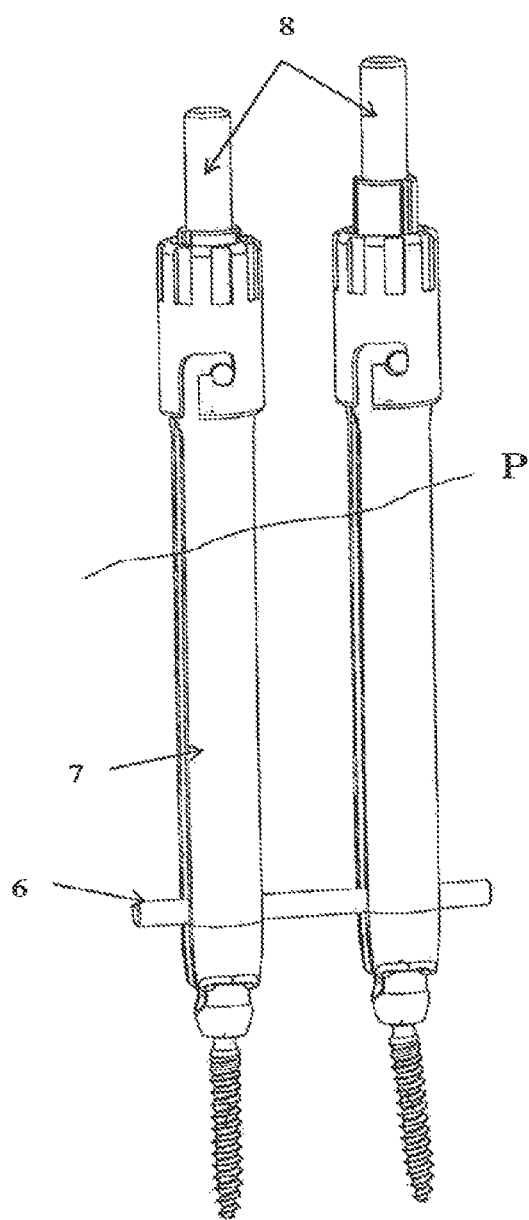

Advantageously, the mounting tube (7) is provided with an aperture (32) in the continuation of the U-shape (25) of the head of the screw (5) in order to allow passage and introduction of the rod (6) (FIGS. 10b and 10c).

Advantageously, the distal portion of the tube (7) is equipped with a thread (35) and a indentation (36). This thread (35) is designed to receive a pushing element (60) of the locking element holding tube (8) and the indentation (36) is designed to receive a perpendicular retaining element (70) (FIG. 10g). The thread (35) is arranged on the surface opposite to the surface on which the indentation is arranged. In the embodiment described, the thread is arranged on the internal surface of distal portion of the tube (7) and the indentation (36) on the external surface of said tube.

The mounting tube (7) is not illustrated in its "one-piece" version, but only in the two preferred embodiments as described below. The external shape of the tube may be of any shape, such as oval or furthermore hexagonal regardless of the version.

Fixing of the tube (7) on the bone anchoring implant (2) may be effected by various designs which are not illustrated. The tube (7) may be made up of 2 arms forming a plier, a fork with its closure system for retention on the implant, or furthermore non-restrictively, of a solid tube and its means of fixing to the implant, wherein the means of connection (21) of the implant are consistent with the design of the tube (7).

FIG. 5 describes a preferred embodiment for the junction between the two half-shells. In this configuration, the two half-shells (30 and 31) are identical and are interconnected by a tenon (33)/mortise (34) device.

In a particular configuration, these two half-shells may be adhesively bonded, soldered, clipped or interlocked, but the preferred embodiment however involves a junction by means of an additional ring (40) (FIGS. 4a and 4b).

In this case, it is the ring that receives the thread (35) and the indentation (36) provided at the distal end of the mounting tube (7). Advantageously, the internal shape of the ring corresponds to the external shape of the mounting tube (7) made up of the two half-shells in this case.

Advantageously, in a first preferred embodiment, the ring is provided with at least one bayonet (41) in the thickness of the ring (40). In order to attach the ring on the mounting tube (7), the latter comprises at least one stud (42) opposite the bayonet(s). In order to maintain the ring (40) in place on the mounting tube (7), a compression spring not illustrated is interposed between the two elements. Assembly and disassembly of the ring and the two half-shells are thereby simplified.

In a second preferred embodiment, the ring (40) is fixed by at least one penetrating stud (43). During the tightening forces of the stopper (3), this stud is subjected to the shearing forces between the torque required for tightening the stopper (3) and the counter-torque exerted by the perpendicular retaining element (70) via the indentation (36). Advantageously, the penetrating stud (43) is dimensioned in order to break under the shearing force. Advantageously, the breaking torque depends on the optimum tightening torque of the stopper (3). Advantageously, the ring (40) is separated from the tube (7) when the final tightening of the implant is performed and disassembly of the two half-shells is thus simplified.

Figure 7:
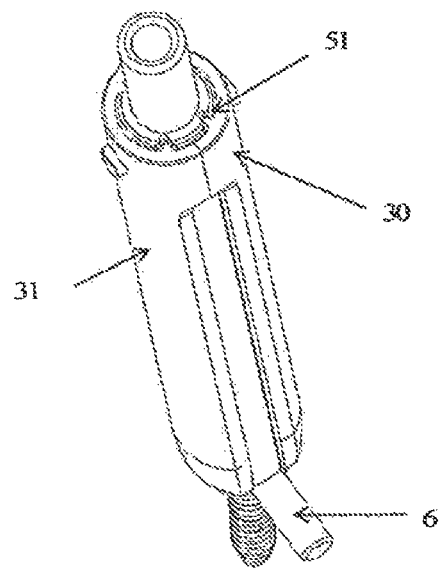
FIG. 7 represents the locking element holding tube inserted into the two half-shells forming the multifunctional mounting tube.

FIGS. 6 and 7 show the locking element holding tube (8) pre-mounted on the stopper (3), in addition to its interconnection in the mounting tube (7) of the screw (2).

The locking element holding tube (8) is arranged in order to securely retain the proximal portion of the stopper (3). The locking element holding tube (8) and stopper (3) unit forms the locking assembly.

Advantageously, the stopper (3) is retained by a tap arranged in the locking element holding tube (8).

According to a preferred variant, this tap is slightly different from the thread of the stopper (3) in order to ensure its retention by trapping.

According to a particular variant, the stopper (3) is retained by a clipping.

Advantageously, the distal end of the locking assembly is equipped with two lugs (50) on either side of the stopper (3), of a length at least equal to the height of the stopper in relation to the latter's face intended to come into contact with the rod (6). The width of these lugs (50) cannot be greater than the diameter of the rod (6). The function of these two lugs is to allow bearing on the rod (6) without any contact of the stopper (3) either on the head of the screw (5) or on the rod (6) until contact of said rod with the interdependence element of the screw (5), i.e. the bottom of the U-shaped channel (25).

According to a preferred configuration, the external shape of the locking element holding tube (8) is provided with at least one dovetail (51) with a shape complementary to the internal shape of the mounting tube (7) of the screw (2). Advantageously, the locking element holding tube (8) is provided with two dovetails (51), one on each half-shell.

These complementary dovetails (51) between the two half-shells (30 and 31) and the locking element holding tube (8) mechanically reinforce the assembly, thereby avoiding any risk of separation or disconnection of the two half-shells under high stresses and impart resistance in flexion and torsion to the assembly.

According to a preferred particular configuration, the total length of the locking element holding tube (8) is greater than that of the mounting tube (7), or furthermore of the two half-shells+ring. It is therefore possible to remove the locking element holding tube (8) once the stopper (3) has been positioned.

According to this particular configuration, the distal portion (52) of the locking element holding tube (8) and the internal shape (62) of the pushing element (60) are compatible for positioning the rod (6) at the bottom of the U-shaped housing (25), the interdependence element of the screw (2). Advantageously, this form (52) is cylindrical.

Advantageously, pushing of the tube (8) by the pushing element (60) may be performed at the end (53) of said tube, or on the shoulder (54) formed by the arrangement of the shape (52).

Advantageously, the internal diameter of the locking element holding tube (8) is designed for passage of the screwdriver.

In the embodiment described, the locking element holding tube (8) therefore also serves as a rod pusher.

Figure 10D:
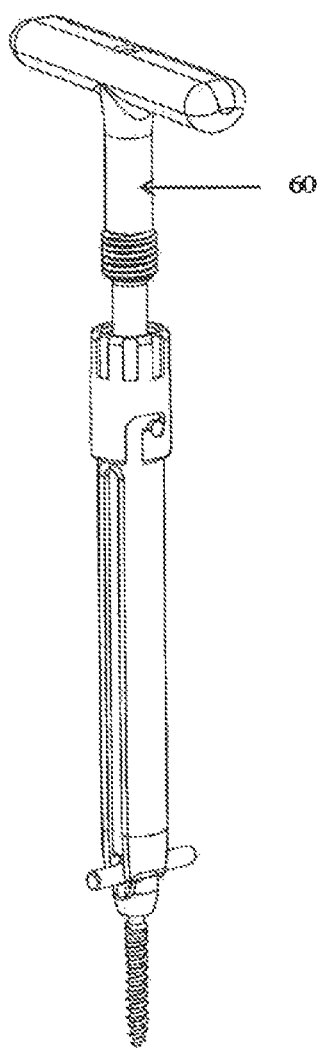
Figure 11:
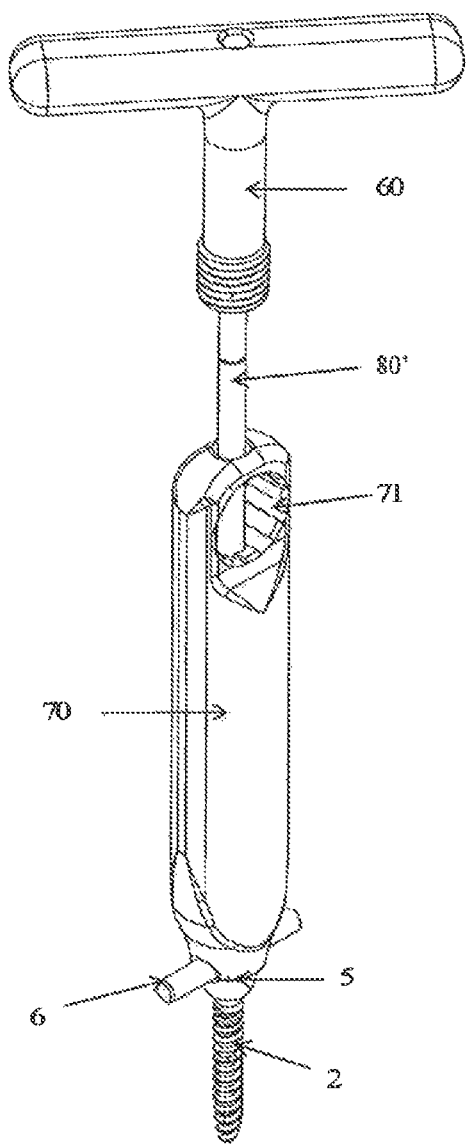
FIG. 11 represents a specific function of the handles during tightening or untightening the locking element when the mounting tube is no longer positioned on the implant.

Advantageously, the pushing element (60) of the locking element holding tube (8)/rod introducer is the T-shaped handle (60) which is equipped with a thread (61) corresponding to that of the distal end of the mounting tube (7) of the screw (2) as shown in FIGS. 8, 10 and 11.

Advantageously, this T-shaped handle is cannulated (63) over its entire length allowing passage of the screwdriver shank of the stopper (80').

According to a particular configuration, this handle (60) is dynamometrically adjusted to the optimum tightening torque of the stopper (3) blocking the rod connecting element (6). Familiar to the person skilled in the art, the torque mechanism is formed of two toothed rings (64) and (65) and a series of "Belleville" washers (66) or a spring.

According to this particular configuration, the proximal meshing portions of the different screwdriver shanks (80 and 80') are different in order to solely allow the torque function on the screwdriver shank intended for tightening the stopper.

According to another particular configuration not illustrated, the screwdriver shank (80') for tightening the stopper (3) has a break initiation in order to break under the tightening force. Advantageously, the breaking torque depends on the optimum tightening torque of the stopper (3). In this particular configuration, the screwdriver shank (80') may be formed in 2 sections longitudinally interconnected; an endpiece with the breakage initiation and the actual screwdriver shank. The endpiece in this case forms an integral part of the locking assembly (8 and 3).

FIG. 9 shows the perpendicular retaining element (70) of the tube (7). One of the ends of this perpendicular retaining element (70) is provided with a indentation (71) complementary with that of the distal end of the mounting tube (7) of the screw (2). In the preferred configuration, the indentation (71) is formed by notches (72). According to different particular embodiments, this indentation (71) may adopt the shape of a hexagon, a polygon or furthermore a hexalobe mentioned by way of example, with the intended purpose being maintenance in rotation of the perpendicular retaining element (70) on the tube (7).

Advantageously, this perpendicular retaining element (70) also constitutes a straight handle and is capable of receiving the different screwdriver shanks (80 and 80'). a indentation (73) is arranged accordingly.

It may be advantageous to also provide a means of retention of the screwdriver shanks (80 and 80') in this handle (70). In the preferred configuration, this retention is performed by an O-ring (74) of a shape and size compatible with the diameters of the screwdriver shanks (80 and 80'). This retention may also be performed by any elastic shape, such as a tongue for example (not illustrated).

Advantageously, a complementary indentation (76) is arranged on the side of the handle, when the latter is considered in its straight position (one will subsequently refer to the straight handle) in order for the latter to be used as a T-shaped handle compatible with the screwdriver shanks (80 and 80').

According to a preferred configuration, one of the ends of this straight handle (70) is provided with a complementary shape (75) to the external shape of the head of the screw (5).

This straight handle therefore allows, during tightening or untightening of stopper, exertion of a counter-torque effect both when the mounting tube (7) is in position and when the latter is disassembled.

Advantageously, this straight handle is cannulated over its entire length allowing passage of the screwdriver shank of the stopper (80').

According to a particular configuration, the handle is arranged in order to securely retain the tightening stopper (3) in its end near the complementary shape (75) to the head of the screw (5). This possibility allows positioning of the stopper (3) in the screw (2) if the mounting tube (7) is not in position.

Advantageously, this retention is performed by a tap (76) of identical shape to the stopper (6), or slightly different in order to ensure retention of said stopper (6) by trapping.

According to another particular variant, the stopper is retained by a clipping.

FIGS. 10a to 10g and 11 describe the different surgical steps of the invention (the vertebrae are not illustrated for reasons of simplicity):

FIG. 10a represents positioning of the screw device (1) in the vertebrae. The handle (70) and the screwdriver shank (80) are used for screwing. A complementary ring not illustrated may be used for attaching all these elements, by means of the thread (35) of the screw device (1).

FIG. 10b represents two screw devices (1) with positioning of the rod (6) in distal portions of the mounting tubes (7) which are advantageously located outside the patient's wound beyond the skin represented hereby the line (P).

FIG. 10c represents insertion of the rod (6) through the two mounting tubes (7). This downwards manoeuvre of the rod may be performed either using the locking element holding tubes (8) or by means of scissors-type or another type of rod holding plier. In this second configuration, the scissors-type rod holding plier not illustrated retain the rod approximately in its centre such as to pass between the two mounting tubes (7).

FIG. 10d represents pushing of the rod (6) into the U-shaped channel of the screw (2) by means of the handle pushing element (60). The thread (61) located in the proximal portion of the handle (60) allows exertion of high pushing forces, whereas the dovetails located in the tubes (7) and (8) reinforce the assembly in torsion and flexion. For this insertion step of the rod (6), the retaining element (70) (not illustrated) may be used perpendicularly in order to counteract the torque transmitted for pushing, thereby obtaining much better control of the surgical procedure.

FIG. 10e represents the rod (6) in position at the bottom of the U shape (25) of the head of the screw (5). The stopper (3) is not yet engaged in the head of the screw (5) and is pre-mounted on the locking element holding tube (8).

FIG. 10f represents positioning of the stopper (3) on the head of the screw (5) by means of the straight handle (70) and the stopper screwdriver shank (80').

FIG. 10g represents the step of final fixing of the rod (6) in the screws (2). The retaining element (70) perpendicularly provides the counter-torque and retention of the assembly; the T-shaped handle (60) and the stopper screwdriver shank (80') allow exertion of the tightening torque of the stopper (3). As described above, measurement of the torque required for optimum tightening may be obtained either by breaking the ring (40), or by means of the torque-type T-shaped handle (60), or furthermore by breaking the screwdriver shank (80').

FIG. 11 likewise represents the final tightening step if the mounting tube (7) is not in position on the screw (2). Indeed for anatomical and dimensional reasons, the surgeon may have cause to disassemble the tube during surgery. This eventuality is rare, but sometimes necessary for proper conduct of surgery. In this configuration, counter-torque retention of the head of the screw (5) is provided by the handle (70) advantageously equipped with a shape complementary to said head of screw (5) as described above. The torque-type T-handle (60) and the stopper screwdriver shank (80') allow exertion of the stopper tightening torque necessary for a good hold of the implant. In this configuration, the mounting tube (7) may be used as a counter-torque perpendicular handle by means of the indentation (71) (not illustrated).

Advantageously, this configuration is used for untightening the stopper, for removing the implants or for any other surgical step requiring separation of the connection between the screw (2)/rod (6).

Advantageously, in order to reduce the number of instruments required for insertion of the implants, the compression and distraction plier only form a single pair of plier. In the state of the art, these pliers are made up of two articulated arms, with the proximal portions of these pliers being formed of forks overlapping the rod (6), said same forks exerting the desired compression/distraction forces on the implants.

Figure 12:
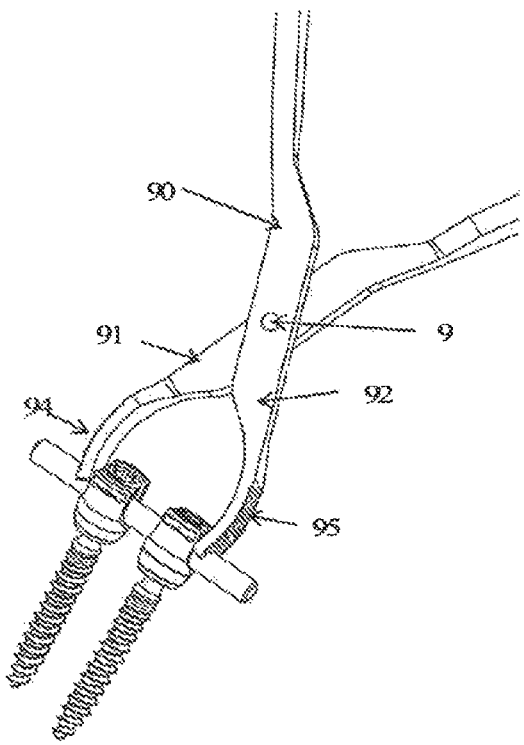
FIG. 12 represents a diagrammatic view of the plier for compression/distraction of the bone anchoring elements in the compression version.

FIG. 12 represents the compression plier (90). This plier mainly consists of two arms (91) and (92) and a joint (93). Each arm (91) and (92) is equipped with a curved end (94) and (95) ending in said fork shape.

Advantageously, the joint (93) is easily removable.

Figure 13:
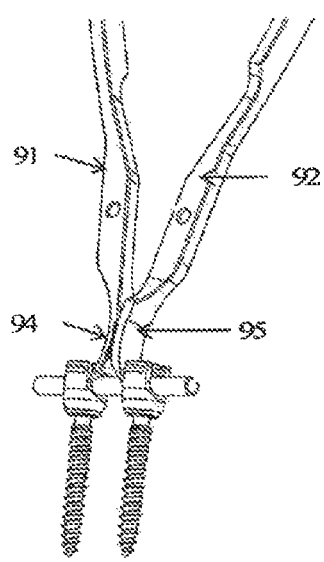
FIG. 13 represents a diagrammatic view of the plier for compression/distraction of the bone anchoring elements in the distraction version.

FIG. 13 represents these same arms (91) and (92) used for a distraction manoeuvre. Advantage is taken of the curved shape of the two curved proximal ends (94) and (95) so that the latter are able to "roll" on each other, thereby exerting the distraction force between the screws (2) by compression of both arms (91) and (92).

In the preferred configuration, two curved proximal ends (94) and (95) include notching in their convex portions in order to prevent frontal sliding of the two arms (91) and (92).

Figure 14:
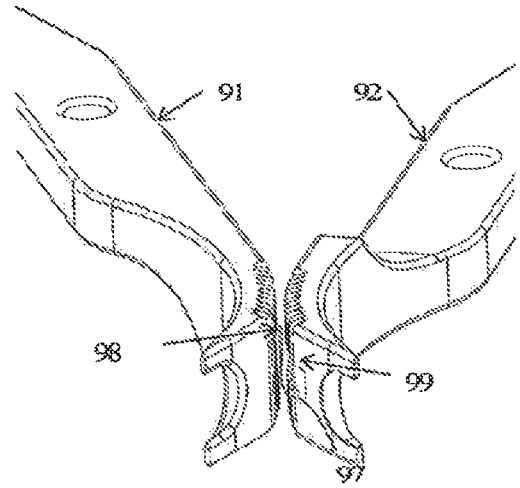
FIG. 14 represents a specific means of joint of this plier in the distraction version.

Advantageously, as illustrated in FIG. 14, the two curved proximal ends (94) and (95) comprise a means (97) of interconnection in order to prevent lateral sliding of the two arms (91) and (92).

In the preferred configuration, this interconnection consists of a stud (98) arranged in one of the curved proximal ends (94) or (95) and a groove (99) arranged in the other curved proximal end.

Figure 15:
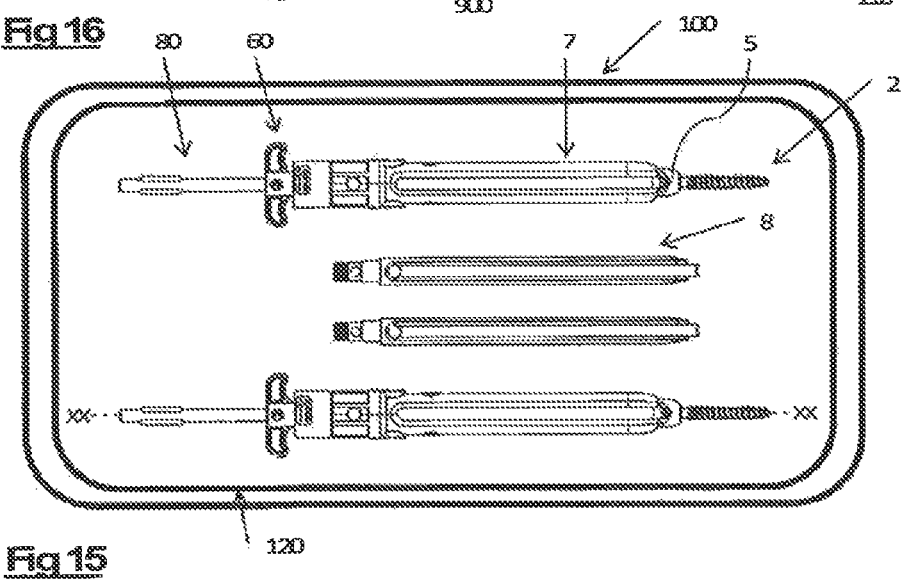
FIG. 15 represents a diagrammatic view of a device according to a second embodiment of the invention.

FIG. 15 describes a device (100) for performing spinal stabilisation according to a second embodiment. In this embodiment, the device (100) comprises two bone anchoring elements (2) interdependently pre-mounted on mounting tubes (7) and two locking elements designed to lock the connecting rod (6) on the bone anchoring element, said locking elements being pre-mounted on tightening tubes (8). Advantageously, the tubes (7) comprise a screwdriver (80).

The arrangement of these elements will be described further below, in relation with FIGS. 20, 21a and 21b.

The set of tubes/screwdriver/screw and tubes/locking elements are arranged in a sealed packaging (120), for sterile and disposable packing.

The set thus packed forms a bone anchoring kit, making available two bone anchoring elements and two locking elements for performing spinal stabilisation using a connecting rod.

It is of course obvious that provision can be made for bone anchoring kits comprising more than two bone anchoring elements and two locking elements pre-mounted on tubes as described above without as a result departing from the field of the invention.

Figure 16:
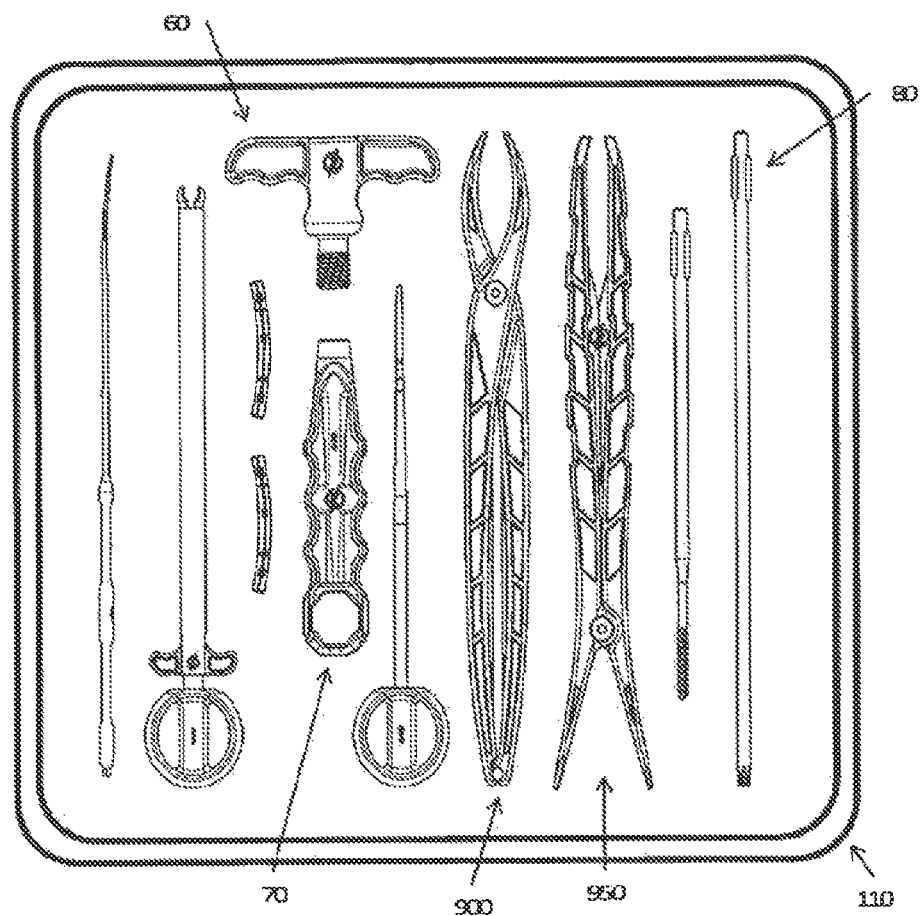
FIG. 16 represents a diagrammatic view of a kit of instruments according to a second example of embodiment of the invention.

FIG. 16 describes a kit of instruments (110) for insertion or removal of implants according to a second example of embodiment of the invention. As in the example of embodiment previously described (FIG. 2), the kit of instruments (110) is for disposable use, sterile packed.

In the embodiment illustrated, the kit of instruments (110) comprises instruments for preparation of pedicle holes (spatula, tap sensor), in addition to instruments required for implantation of the pedicle screws and connecting rods (screwdriver shank 80, plier 900, 950 and handles 60, 70). It should be noted that the plier (900, 950) present in the kit of instruments (110) have a dual functionality which will be described below.

The kit of instruments (110) reiterates the set of characteristics for the kit of instruments (10) previously described.

Figures 17, 18, 19:
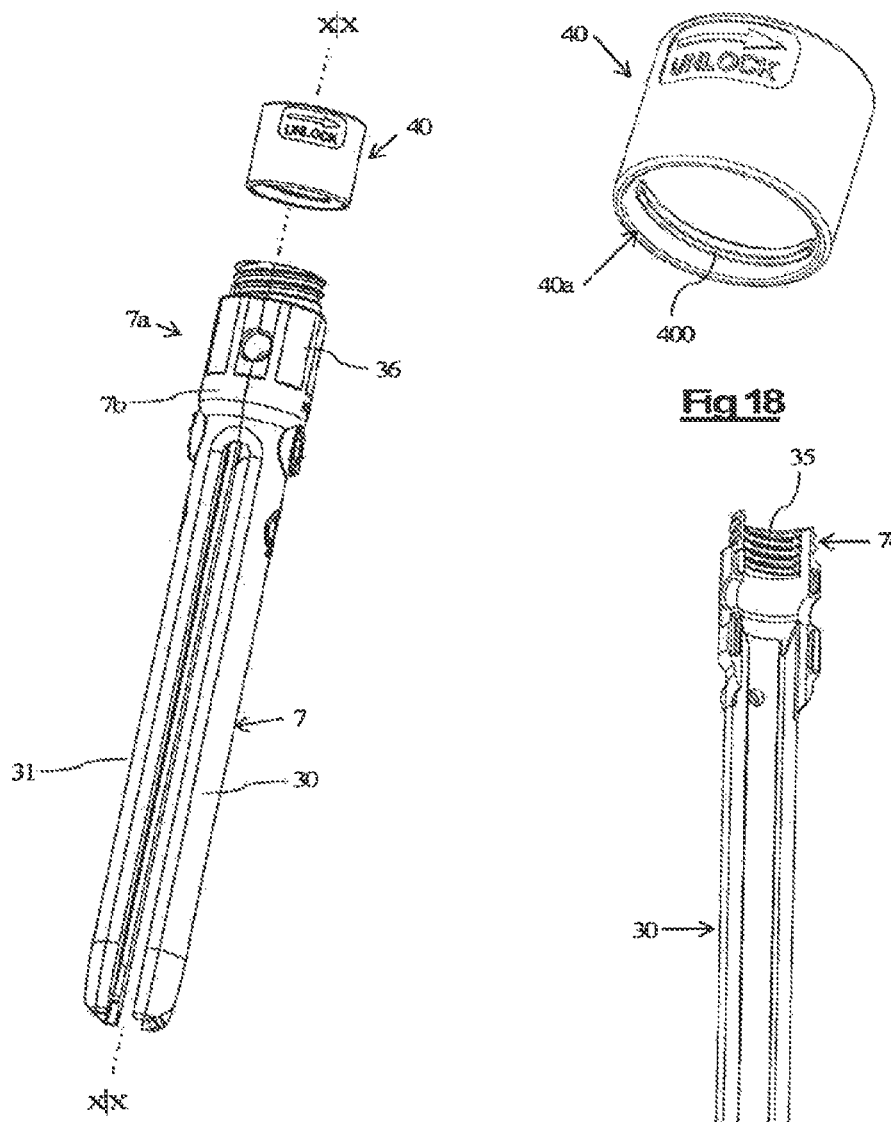
FIG. 17 represents a diagrammatic view of the mounting tube and the ring forming the device in FIG. 15, said ring being illustrated unassembled on the mounting tube.
FIG. 18 represents a bottom view of the ring in FIG. 17.
FIG. 19 represents a cross-sectional view along the axis XIX-XIX of the mounting tube in FIG. 17.

FIGS. 17 to 19 represent views of a tube (7) and a retaining ring (40) forming the device in FIG. 15. The tube (7) reiterates the set of characteristics of the tube previously described. In the example illustrated in FIG. 15 however, the means employed in order to receive a pushing element (or T-shaped handle) (60) in addition to a perpendicular retaining element (70) held, in the example previously described, by the ring 40, are now directly held by the tube (7).

Hence, in the embodiment described, the distal portion (7a) of the tube (7) comprises an external face (7b) provided with the indentation (36) designed to receive the perpendicular retaining element (70) and an internal face (7c) provided with the thread (35) to receive the pushing element (60). In the embodiment described and in the previous example, the indentation is hexagonal in shape.

Advantageously, the distal portion (7a) of the tube (7) comprises, in the extension of the indentation (36) an external thread (7d) capable of interacting with at least one tongue (400) of complementary shape arranged on the internal face (40a) of the ring (40), thereby allowing fixing of the ring on the distal end of the tube (7). In this example of embodiment, the sole function of the ring (40) is to maintain the two half-shells (30, 31) in relation to one another.

Advantageously, the external thread arranged on each half-shell (30, 31) is comprised of a double screw thread in order to ensure that the thread is identical on each half-shell such that the thread resulting from the junction of the threads of the two half-shells is continuous.

Advantageously, the ring (40) has an external diameter smaller than the nominal diameter of the indentation (36) when the two half-shells (30, 31) are in position in order to form the tube (7). The aim of this specific dimensioning of the ring (40) is to allow passage of the perpendicular retaining element (70) for its position at the level of the indentation (36).

Figure 22:
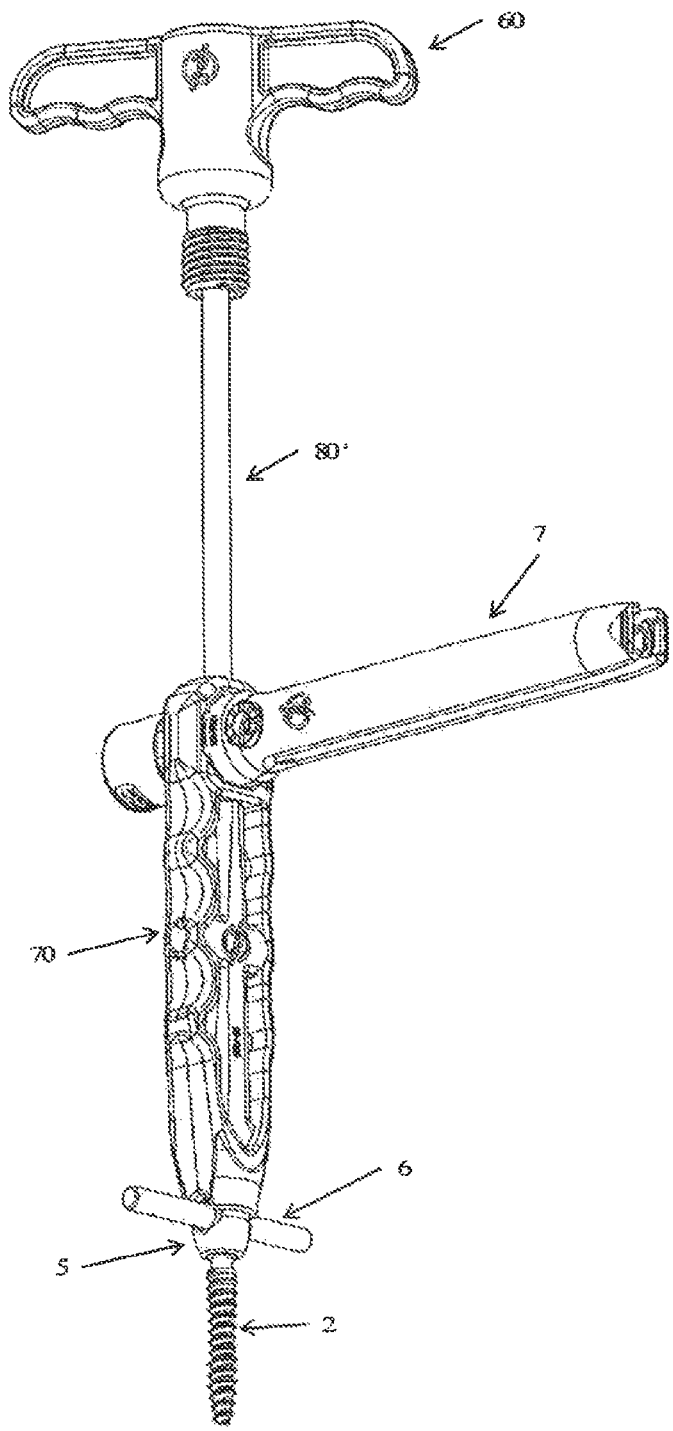
FIG. 22 represents a diagrammatic view of a tube/screwdriver/handle assembly according to a variant of use.

Advantageously, the distal portion (7a) comprises a hole (700) arranged at the level of the indentation (36) in order to allow passage of a screwdriver shank (80, 80') when the retaining element (70) is used as a substitute for the tube (7), as illustrated in FIG. 22. In this illustrated embodiment, the tube (7) is used as a replacement for the retaining element (70), with the tube thereby functioning as a handle and the retaining element (70) as a replacement for the tube (7).

FIG. 20 illustrates a cross-sectional view along the axis XX-XX of the mounting tube/screwdriver/anchoring element assembly illustrated in FIG. 15.

As illustrated in FIGS. 20 and 21a, the screwdriver shank (80) is pre-mounted on the anchoring element (2). More specifically, the proximal end (80a) of the screwdriver shank (80) is arranged in order to interact with the screw (2). Advantageously, the assembly comprises means allowing the screwdriver shank (80) to be maintained in the axis of the threaded portion (4) of the anchoring element (2). By way of a non-restrictive example, the means of maintaining the screwdriver shank (80) in the axis of the bone anchoring element comprise lugs (800) arranged on the internal face of the tube (7).

As illustrated in FIGS. 20 and 21b, the assembly advantageously comprises a retaining fin (60') for maintaining the screwdriver shank 80 in a given position in relation to the tube (7) and the screw (2).

The retaining fin (60'), which is T-shaped, is pre-mounted on the distal end of the tube (7). Its bottom part comprises a thread (61') corresponding to the tap (35) of the distal portion of the tube (7).

Advantageously, the retaining fin (60') comprises, over its entire length, a channel through which the screwdriver shank (80) passes.

The retaining fin (60') is arranged in order to ensure axial retention of the screwdriver shank (80) in the tube (7) while allowing a rotational movement of the shank inside the tube (7) in order to allow imparting of rotation to the threaded portion (4) of the screw (2), with the head (5) of the screw remaining immobile in relation to the shank.

According to an advantageous embodiment, it is arranged in order to keep the alignment of the screwdriver shank (80) in the alignment of the bone anchoring element (2).

Owing to preassembly at the factory of the screwdriver shank (80) on the screw which is also pre-mounted in a tube (7), reduced tolerance is allowed and consequently better retention of the screw according to the flexion forces is ensured.

A preassembly of this kind also has the advantage of allowing on the one hand a saving in surgery time, with the operation of positioning the screwdriver shank on the bone anchoring element being eliminated and on the other hand a limitation in the surgical risk, since the duration of anaesthesia is reduced.

Such a preassembly also has the advantage of avoiding any problems in pairing the screwdriver shank/screw.

In the same manner as in the embodiment illustrated in FIG. 11, the tube (7) can be used as a perpendicular handle and the perpendicular handle (70) as a guide tube of a stopper screwdriver shank (80') (FIG. 22).

FIGS. 23a and 23b represent a compression plier (900) contained in the kit of instruments (110). The compression plier (900), which has a plane of symmetry P, comprises two arms (910), (920) mounted articulated in relation to each another. In the embodiment described, the arms are arranged crossed in relation to each another.

As for the compression plier described above (FIG. 12), each arm (910, 920) has a fork-shaped curved end (930), wherein the fork-shaped ends (930) of each arm are arranged opposite one another in relation to the plane of symmetry in order to be able to overlap the rod (6). The ends of the arms thus arranged form ends of the plier known as compression ends (930).

Advantageously, the opposite ends (940) to the compression ends (930) are arranged in order to allow gripping the rod (6) by moving the arms (910, 920) towards each other. One will subsequently refer to gripping ends (940) of the plier (900). In order to facilitate gripping, the gripping ends (940) of each arm (910, 920) comprise two fingers defining a space for receiving the rod (6). Hence, when the arms (910, 920) are in the close position, the rod (6) is retained trapped between the fingers of the gripping ends (940) of each of the arms.

Thus configured, the compression plier (900) allows, by means of their compression ends (930), exertion of a compression force on the bone anchoring elements, as illustrated in FIG. 23b and by means of their gripping ends (940), opposite the compression ends, holding of the rod, as illustrated in FIG. 23a. This dual functionality makes it possible to reduce the number of instruments required for insertion of the implant and therefore reduce the number of instruments to be handled accordingly.

In order to reduce the force required to effect compression of the implants, the joint (901) is designed to ensure that the distance between the compression ends (930) and the joint (901) is less than the distance between the gripping ends (940) and the joint (901), with the distance being considered according to the longitudinal axis of the plier.

FIGS. 24a and 24b represent a distraction plier (950) contained in the kit of instruments (100).

In this embodiment, the distraction plier (950), which has a plane of symmetry P', comprises two arms (960), (970) hinged to each other by a joint (951).

Each end (980) of each arm (960, 970), with a fork-shaped configuration, is arranged in order to overlap a rod (6) as illustrated in FIGS. 24a and 24b. Therefore, according to their positioning on the rod (6), depending on whether they are positioned between the two anchoring elements (2) (FIG. 24b) or on either side of the two anchoring elements (2) (FIG. 24a), the ends will be able to exert desired distraction/compression forces on the rod (6). In this case, one will refer to distraction ends (980) or compression ends (990).

This dual functionality makes it possible to reduce the number of instruments required for insertion of the implant and therefore reduce the number of instruments to be handled accordingly.

In order to allow compressions over a wide distance, the joint (951) is designed to ensure that the distance between the distraction ends (980) and the joint (951) is less than the distance between the compression ends (990) and the joint (951), with the distance being considered according to the longitudinal axis of the plier.

Thus configured, the distraction plier (950) allows, by means of their compression ends, exertion of a distraction force on the implants, as illustrated in FIG. 24b and by means of their gripping ends, exertion of a wide compression force, as illustrated in FIG. 24a.

Figures 25A, 25B, 25C:
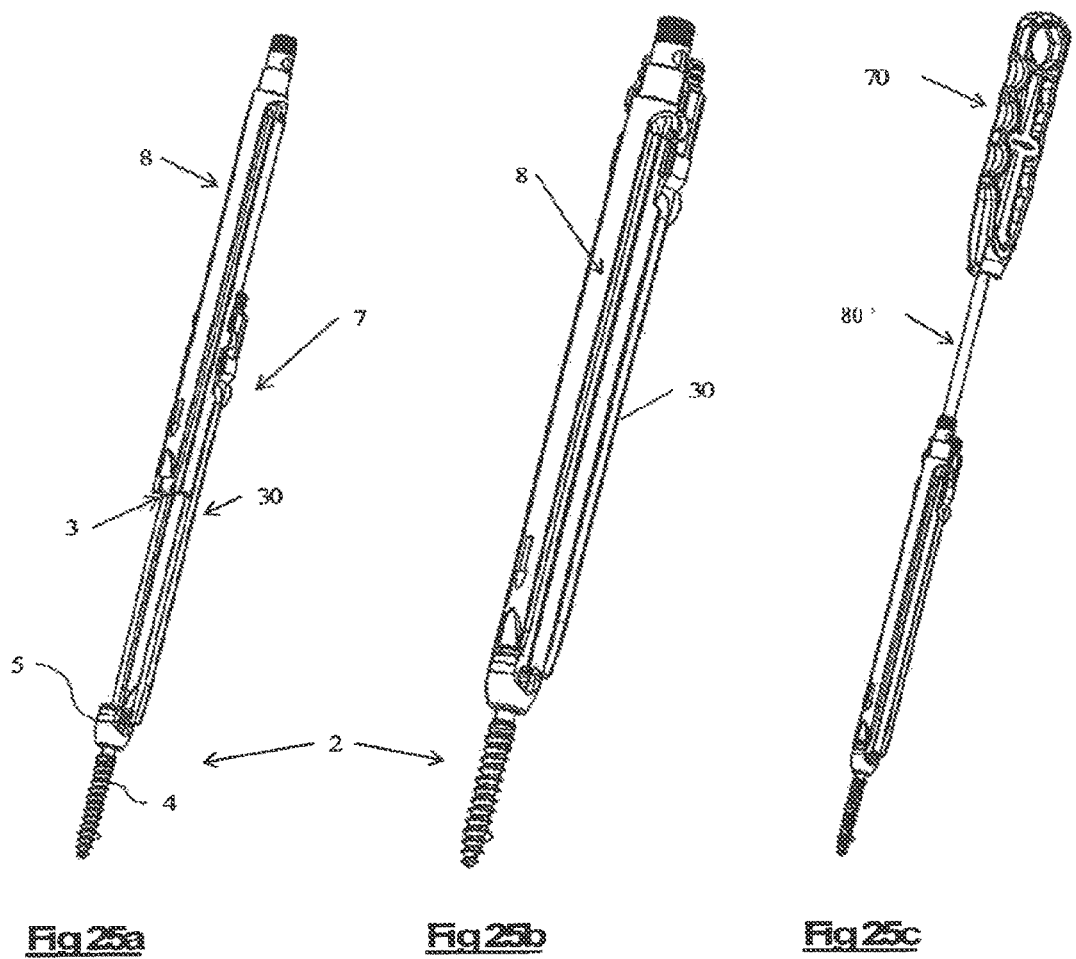
FIGS. 25*a* to 25*c* represent the steps for positioning the locking element when the mounting tube has been disassembled.

FIGS. 25a to 25c illustrate the assembly steps of a stopper (3) on the head (5) of the screw (2) when the mounting tube (7) has been dismantled from the screw (2).

Therefore and as illustrated in FIG. 25a, the tube (8) bearing the stopper (3) is positioned on the head (5) of the screw by sliding the tube (8) along one of the half-shells (30, 31) mounted on the head (5) of the screw. The half-shell (30) thereby allows guiding of the stopper (3) towards the screw head.

Once the tube (8) completely rests in the half-shell (30) (FIG. 25b), the stopper screwdriver shank (80') is inserted into the canal of the locking tube (8) in order to proceed with tightening the stopper (3) on the rod (6) (not illustrated in the figures but present) and on the head (5) of the screw (FIG. 25c).

The embodiment illustrated in FIGS. 25a to 25c is advantageous in the sense that only a single half-shell of the tube (7) is necessary in order to allow guiding and positioning of the stopper (3) on the head (5).

The invention is described above by way of an example. It is understood that the person skilled in the art is capable of producing different variants of embodiment of the invention without departing from the framework of the invention.

The invention claimed is:

1. An instrument kit for installing or removing a rachidian implant, said implant comprising at least two threaded bone-anchoring elements, a connecting element of a rod-type or plate-type mechanically connecting the bone-anchoring elements and locking elements for locking the connecting element in position with respect to the bone-anchoring elements, said instrument kit comprising instruments configured to perform surgical actions relating to the installation or removal of said implant, wherein said instruments being single use instruments and being packaged sterile in at least one sealed package, the single use instruments configured removable from the at least one sealed package at the beginning of the surgical actions and being discarded at the end of the surgical actions without being sterilized again, wherein said implant is not packaged in said instrument kit, wherein said instrument kit comprises a T-shaped handle equipped with a torque limiter located within the T-shaped handle, said torque limiter configured for the final dynamometric tightening of at least one of the locking elements;
further comprising a screwdriver shank for tightening the locking element, said screwdriver shank comprising a coupling extremity for coupling with the locking element and wherein the T-shaped handle is configured to receive said screwdriver shank for tightening the locking element said instrument kit further comprising a straight handle configured to engage with said screwdriver shank while said screwdriver shank is received through the T-shaped handle.

2. An instrument kit for installing or removing a rachidian implant according to claim 1, wherein said instruments are produced from composite material, polymer, ferrous or non-ferrous alloy or a combination thereof.

3. An instrument kit for installing or removing a rachidian implant according to claim 1, further comprising at least one additional screwdriver shank, a handle and a plier.

4. An instrument kit for installing or removing a rachidian implant according to claim 1, wherein the straight handle is for the placing or removal of the bone-anchoring elements, the tightening or slackening of the locking elements, and a perpendicular holding of a spinal device.

5. An instrument kit for installing or removing a rachidian implant according to claim 4, wherein the straight handle also allows use in a T-configuration for placing or removing the bone-anchoring elements and tightening or slackening the locking elements.

6. An instrument kit for installing or removing a rachidian implant according to claim 4, wherein the straight handle enables at least one of the bone-anchoring elements to be held for tightening or slackening the locking elements.

7. An instrument kit for installing or removing a rachidian implant according to claim 4, wherein the straight handle allows gripping of the locking element and guidance thereof on at least one of the bone-anchoring elements.

8. An instrument kit for installing or removing a rachidian implant according to claim 1, further comprising a maneuvering plier comprising two arms allowing compression or distraction of the bone-anchoring elements.

9. An instrument kit for installing or removing a rachidian implant according to claim 8, wherein the maneuvering plier with two arms comprises curved proximal ends with serration on convex parts.

10. An instrument kit for installing or removing a rachidian implant according to claim 8, wherein the maneuvering plier with two arms comprises curved proximal ends with a longitudinal positive location.

11. An instrument kit for installing or removing a rachidian implant according to claim 10, wherein the positive location is implemented by a groove on one of the arms, and a stud projecting on another of the arms.

12. An instrument kit for installing or removing a rachidian implant according to claim 1, further comprising a plier comprising two arms crossed symmetrically with respect to a reference plane and fixed to each other by a hinge, each said arm having an end in the form of a fork for straddling a rod, the fork-shaped ends of each arm being placed facing each other with respect to a symmetry plane, the ends of the arms forming compression ends, and the ends opposite to the compression ends of each said arm being arranged so as to enable the rod to be gripped during a movement in which the compression ends are brought towards each other.

13. An instrument kit for installing or removing a rachidian implant according to claim 1, further comprising a plier comprising two arms symmetrical with respect to a reference plane and joined to each other by a hinge, each said arm having first and second ends in the form of a fork for straddling a rod, one of the ends of one of the arms being arranged with the end of another arm placed opposite thereto and with respect to a symmetry plane in order to form distraction ends, the other ends forming compression ends.

14. An instrument kit for installing or removing a rachidian implant according to claim 1, wherein at least one of said instruments is multifunctional.

* * * * *